(12) United States Patent
Martin et al.

(10) Patent No.: US 11,590,402 B2
(45) Date of Patent: Feb. 28, 2023

(54) AUTOMATED PHYSICAL TRAINING SYSTEM

(71) Applicant: The Quick Board, LLC, Memphis, TN (US)

(72) Inventors: Kevin L Martin, Memphis, TN (US); Jason Fisher, Germantown, TN (US); Daniel Ilinca, Vlontari (RO)

(73) Assignee: The Quick Board, LLC, Arlington, TN (US)

( * ) Notice: Subject to any disclaimer, the term of this patent is extended or adjusted under 35 U.S.C. 154(b) by 875 days.

(21) Appl. No.: 16/428,658

(22) Filed: May 31, 2019

(65) Prior Publication Data

US 2020/0054931 A1 Feb. 20, 2020

Related U.S. Application Data

(60) Provisional application No. 62/678,923, filed on May 31, 2018.

(51) Int. Cl.
*A63B 71/06* (2006.01)
*G06F 16/95* (2019.01)
(Continued)

(52) U.S. Cl.
CPC ...... *A63B 71/0622* (2013.01); *A63B 24/0062* (2013.01); *A63B 24/0075* (2013.01);
(Continued)

(58) Field of Classification Search
CPC ............ A63B 71/0622; A63B 24/0062; A63B 24/0075; A63B 71/0686; A63B 2024/0068; A63B 2071/065; A63B 2220/53; A63B 2220/56; A63B 2220/62; A63B 2220/806; A63B 2220/836; A63B 2225/52; G06F 3/011; G06F 3/0334; G06F 16/95; G06F 2203/012; G06T 7/20; G06T 2207/10016; G06T 2207/30196; G06T 2200/24; G06T 2207/30221; G06T 7/248; G06T 7/254; A61B 5/1038; A61B 5/6807; A61B 2505/09; A61B 5/1118; A61B 5/112; A61B 5/1128; A61B 5/486; A61B 5/6892; G09B 5/02; G09B 19/0038
See application file for complete search history.

(56) References Cited

U.S. PATENT DOCUMENTS 5,720,200 A * 2/1998 Anderson ............ A61B 5/1036
73/172
6,336,891 B1 * 1/2002 Fedrigon ............ A63B 24/0006
482/4

(Continued)

*Primary Examiner* — Sundhara M Ganesan
(74) *Attorney, Agent, or Firm* — Baker Donelson

(57) ABSTRACT

Systems, methods and computer readable media comprising a virtual exercise board, which is represented by images on the screen of a pad device; wearable devices configured to attach to each shoe of a user and to collect and transmit touch data to the pad device; cameras for tracking movement and calibrating with the data collected by the wearable devices; and computer programs for collecting user data, processing user data, and generating outputs. In embodiments, features include augmented reality; ratings of performance; automated workouts/protocols; real-time progress bar; multi-location database capabilities; and reports.

12 Claims, 37 Drawing Sheets

(51) Int. Cl.
*A63B 24/00* (2006.01)
*G06F 3/01* (2006.01)
*G06F 3/033* (2013.01)
*G06T 7/20* (2017.01)
*A61B 5/103* (2006.01)
*A61B 5/00* (2006.01)

(52) U.S. Cl.
CPC .......... *A63B 71/0686* (2013.01); *G06F 3/011* (2013.01); *G06F 3/0334* (2013.01); *G06F 16/95* (2019.01); *G06T 7/20* (2013.01); *A61B 5/1038* (2013.01); *A61B 5/6807* (2013.01); *A63B 2024/0068* (2013.01); *A63B 2071/065* (2013.01); *A63B 2220/53* (2013.01); *A63B 2220/56* (2013.01); *A63B 2220/62* (2013.01); *A63B 2220/806* (2013.01); *A63B 2220/836* (2013.01); *A63B 2225/52* (2013.01); *G06T 2207/10016* (2013.01); *G06T 2207/30196* (2013.01)

(56) References Cited

U.S. PATENT DOCUMENTS

| | | | | |
|---|---|---|---|---|
| 6,685,480 | B2* | 2/2004 | Nishimoto | G09B 15/00 482/8 |
| 7,060,000 | B2* | 6/2006 | Carlson | A63B 69/0053 434/258 |
| 8,253,586 | B1* | 8/2012 | Matak | G01L 5/0095 340/870.07 |
| 8,827,815 | B2* | 9/2014 | Burroughs | G16H 20/30 702/182 |
| 9,429,411 | B2* | 8/2016 | Meschter | H04N 7/181 |
| 9,553,873 | B2* | 1/2017 | Agnew | H04L 67/06 |
| 11,172,818 | B1* | 11/2021 | Theimer | G06T 7/20 |
| 11,210,834 | B1* | 12/2021 | Chamdani | G06T 13/40 |
| 11,221,493 | B1* | 1/2022 | Baker | G06F 3/017 |
| 2001/0016510 | A1* | 8/2001 | Ishikawa | A63F 13/40 463/7 |
| 2005/0153265 | A1* | 7/2005 | Kavana | G10H 1/368 434/250 |
| 2006/0258512 | A1* | 11/2006 | Nicolas | A63B 21/00 482/52 |
| 2006/0266200 | A1* | 11/2006 | Goodwin | A63F 13/814 84/611 |
| 2007/0079690 | A1* | 4/2007 | Chiwata | G10H 1/368 84/609 |
| 2008/0004111 | A1* | 1/2008 | Prather | A63F 13/06 463/36 |
| 2008/0102991 | A1* | 5/2008 | Hawkins | A63B 69/0053 473/422 |
| 2008/0146329 | A1* | 6/2008 | Kodama | A63F 13/214 463/31 |
| 2009/0221372 | A1* | 9/2009 | Casey | A63F 13/212 463/36 |
| 2010/0204615 | A1* | 8/2010 | Kyle | G01C 22/006 600/595 |
| 2012/0122588 | A1* | 5/2012 | Berger | A63F 13/80 463/42 |
| 2013/0224708 | A1* | 8/2013 | Martin | G09B 19/00 434/247 |
| 2019/0188868 | A1* | 6/2019 | Bagnall | G06T 7/75 |
| 2021/0307650 | A1* | 10/2021 | Barr | A61B 5/0022 |
| 2021/0334546 | A1* | 10/2021 | Zhang | G16H 40/63 |
| 2022/0001272 | A1* | 1/2022 | Ohashi | A63F 13/22 |
| 2022/0011869 | A1* | 1/2022 | Lawrence | G06F 3/011 |
| 2022/0023718 | A1* | 1/2022 | Augustin | G06F 3/04815 |
| 2022/0057424 | A1* | 2/2022 | Bieglmayer | G01C 25/005 |
| 2022/0066544 | A1* | 3/2022 | Kwon | G06F 3/011 |
| 2022/0101588 | A1* | 3/2022 | Garofalo | G06F 3/01 |
| 2022/0134181 | A1* | 5/2022 | Fung | A63F 13/65 482/8 |
| 2022/0139047 | A1* | 5/2022 | Lowe | H04W 4/38 345/633 |
| 2022/0143483 | A1* | 5/2022 | Liu | A61B 5/1118 |
| 2022/0147148 | A1* | 5/2022 | Begley | G06F 3/011 |

* cited by examiner

AUTOMATED PHYSICAL TRAINING SYSTEM

CROSS REFERENCE TO RELATED APPLICATIONS

This application claims priority to U.S. Provisional Patent Application 62/678,923, filed May 31, 2018, which is incorporated herein by reference in its entirety.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent files or records, but otherwise reserves all copyright rights whatsoever.

FIELD OF THE INVENTION

The present disclosure relates to methods, systems and computer readable media for providing physical training and physical rehabilitation. More particularly, the present disclosure relates to methods, systems and computer readable media for using wearable devices to provide, track and analyze physical performance on certain exercises, as well as for analyzing training results and providing patient specific training recommendations based on performance over periods of time.

BACKGROUND OF THE INVENTION

The inventor previously developed a system for physical training using a particular type of sensor board. This system is described in U.S. Patent Application Publication 2013/0224708A1 (Martin), which is incorporated herein by reference in its entirety, and is marketed as the QUICK BOARD® system. The QUICK BOARD® system uses a pad that has five target sensors. A computer system interacts with the pad and a display panel to receive inputs from the user and to transmit instructions to the display panel for use in performing athletic training and physical therapy exercises.

The QUICK BOARD® system has had great success improving the performance of athletes and with rehabilitating patient's suffering from Parkinson's and other conditions. For example, one study concluded that the system increased a training group's agility in a laser timed, change-of-direction drill. *The Journal of Strength and Conditioning Research* (22(6): 1901-1907, November 2008).

Despite the success of the QUICK BOARD® system, the inventor has identified areas for improving the QUICK BOARD® system, including improving upon the teachings of U.S. Patent Application Publication 2013/0224708A1.

OBJECTS AND SUMMARY OF THE INVENTION

It is an object of the inventions to provide improved methods, systems and computer readable media for providing physical training and physical rehabilitation.

It is another object of the inventions to provide methods, systems and computer readable media for using wearable devices to provide, track and analyze physical performance on certain exercises.

It is another object of the inventions to provide methods, systems and computer readable media for using wearable devices to analyze training results and provide patient specific training recommendations based on performance over periods of time.

It is yet another object of the inventions to provide exercise systems that improve on existing systems by incorporating augmented reality and wearable devices.

The foregoing objectives and others are achieved by providing systems, methods and computer readable media having the features described herein.

The invention includes systems, methods and computer readable media including, generally, a virtual exercise board, which is represented by images on the screen of a pad device, such as an iPad®; wearable devices configured to attach to each shoe of a user and to collect and transmit touch data to the pad device; cameras for tracking movement and calibrating with the data collected by the wearable devices; and computer programs for collecting user data, processing user data, and generating outputs. In embodiments, features include Augmented Reality; Ratings of performance; Automated workouts/protocols; Real-time Progress Bar; Multi location database capabilities; and Reports.

The wearable devices are configured for executing a physical training routine and collecting user data during the routine. The camera systems are configured for executing an augmented reality physical training routine and collecting user data during the routine. The camera system for executing augmented reality physical training routines can be combined with: a video processing algorithm for tracking said user's shoes, the algorithm for tracking said user's shoes comprising tracking-learning-detection; and a video processing algorithm for detecting the presence of said user's shoes on the sensor area, said algorithm for detecting the presence of said user's shoes on the sensors area using background change.

In embodiments, the inventions include a wearable device in combination with a camera system for executing a physical training routine and collecting additional user metrics such as Cadence; Foot strike; Pressure; Impulse; Impact force; Contact time; Air time; Pronation; Supination.

In embodiments, the inventions include methods implemented by a processor for providing physical training routines for a user as described herein. In embodiments, the inventions include a computer readable medium for providing physical training routines for a user as described herein.

In embodiments, the inventions include a system for providing physical training routines for improving a user's health and functional performance, the system comprising based on artificial intelligence using population data and/or personal data collected by a wearable device.

A wearable device is provided for each shoe of a user. The wearable device can be configured to clip to the shoes, collect user data during exercises, and transmit the data to the pad device. In embodiments, the wearable device is a sub-insole device that sticks to the bottom of an insole of each shoe of a user. The wearable may include one or a plurality of sensors that are distributed on the bottom of a shoe insole so as to detect pressure and touches at selected parts of the foot. The shoe insole can be an insertable orthotic. The sensors are attached to the bottom of the insole, such as by tape or an adhesive. In embodiments, the plurality of sensors includes one, two, three, four or five sensors. The individual sensors are configured to sense pressure. The sensors can be pressure sensors, bend sensors, and the like. In embodiments, the sensors are electrically coupled by a bridge to a component housing. The component housing encloses and protects a collection of wearable operative components that are configured to collect user data and transmit the data to the system during use of the exercise programs. The operative components in the housing include a circuit board having a processor, a battery, and a transmitter. The operative components can include orientation components such as an accelerometer; an accelerometer and gyroscope; or an accelerometer, gyroscope and magnetometer. Adding orientation components to the circuit board gives additional data points in addition to the data collected from the sensors and camera, which enables additional capabilities.

The operative components sync user data to the display pad, which in turn syncs the data to the system. In embodiments, the operative components transmit the data via blue tooth low energy (BTLE). The battery may be chargeable, such as through a conventional electrical outlet, by wireless charging, and the like.

The bridge between the sensors and the component housing can be an elongated cable, such as a flat cable. A shoe attachment means can be provided on the component housing, such as a clip or other mechanism for selectively and removably attaching the component housing to the shoe of a user. In embodiments, the attachment means can include a pouch that attaches to the shoe and is sized to securely receive the component housing.

The inventions include a computer readable medium with an augmented reality calibration process, including the flow and function of a Calibration stage of the application described herein. Calibration activity is an important step for processing algorithms, requiring some technical positioning of the tablet. For example, when using a 12.9 inch tablet, the following are recommended: the tablet should be at a height of 63 inches; the tablet angle is between 80 and 83 degrees. When using a 9.7 inch or 10.9 inch tablet, the following are recommended: the tablet should be at a height of 63 inches; the tablet angle is between 70 and 73 degrees.

In embodiments, calibration routines are used to more accurately show the user where his or her feet are in relation to the virtual board shown on the screen. In the agility drill with AR and insoles, the system is able to track whole body movement as well, not just sensor areas seen by the camera. If the user moves out of the arrows and moves out of the screen area and come back in the screen, calibration times the amount of time between loss of sight and when it comes back into the camera.

The Agility Drill functions differently than the Count, Sequence, React, and Vertical drills. For Count, Sequence, React, and Vertical drills, the user stays in the camera view with augmented sensor areas displayed around them. For the Agility Drill, a single sensor location is displayed in the middle of the screen which marks the area where a user should stand. During an Agility Drill, an arrow appears on the screen, then a user will leave the sensor location within the camera's view to move to a predetermined location outside of the camera view, which starts a timer. Once the user has moved to the predetermined location, outside of the camera view, identified by cones, tape, and other types of physical markers, and returns to the sensor location within the camera's view, the timer stops. At this point, the user will wait for the next arrow to appear then the timing process will repeat. Agility Drill with Augmented Reality provides objective movement times to the user and communicates whether they are improving their agility performance.

In embodiments, the inventions include a system for providing physical training routines for a user, the system comprising: a wearable device for executing a physical training routine and collecting user data during the routine; and a camera system for executing an augmented reality physical training routine and collecting user data during the routine, the camera system for executing augmented reality routines combined with video processing algorithms. (1) Tracking-learning-detection, which is used for tracking user's shoes; (2) Background change, which is used for detecting the presence of shoes on sensors area.

A wearable device in combination with a camera system for executing a physical training routine and collecting additional user metrics such as Cadence; Foot strike; Pressure; Impulse; Impact force; Contact time; Air time; Pronation; Supination.

In embodiments, ratings are incorporated into the systems, methods and computer readable media. A rating generator uses algorithms based on user performance or rehabilitation data to provide a composite score of one or more exercises compared to data in the database. Ratings are based on a user's exercise results or a rating is provided based on a specific assessment protocol. Ratings can be wholly or partially based on data gathered during uses, such as data gathered from a user or users wearable insoles. After a user receives a rating, the system's artificial intelligence recommends a physical training plan for the user in order to improve a user's rating. Types of ratings can include:

Symmetry rating takes contact times, reaction times and paired exercise results into consideration to come up with a rating based on all of those data points.

Stability Rating based on foot pressure data recorded by an insole device.

Injury rating is based on a user's exercise results, overall rehabilitation progress and/or assessment protocol compared to similar population data and injury data in the database.

Predictive Outcome Rating predicts user rehabilitation outcome based on the user's overall rehabilitation progress compared to similar population data and injury data in the database.

Training Progress Rating based on a user's overall progress compared to similar population data.

Rehabilitation Progress Rating is based on a user's overall progress compared to similar population data and injury data.

Surgical Procedure Rating is based on a user's overall rehabilitation progress compared to similar population data, injury data, and surgical procedure data.

Outcome Rating is generated based on a user's final rehabilitation phase results compared to final rehabilitation phase population norms.

Neurodegenerative Disease Rating is based on a user's assessment protocol results compared to similar population data which includes diagnosed neurodegenerative disease.

Agility rating is based on a user's assessment protocol results which includes reaction, coordination, proprioception, speed, and quickness exercises and is compared to database results. Screens can be provided for an agility rating summary and an agility rating report.

Preparedness rating is displayed after an athlete performs a Double Leg React exercise and is based on the standard deviation over the past results of Double Leg React exercises for that athlete.

Return to Play Rating compares user's rehabilitation results or assessment results to similar patient population data to convey whether a user is ready to return to play.

Reaction Rating based on one or more reaction or neurocognitive reaction exercise or assessment results to monitor nervous system function.

Injury Exposure Rating evaluates a user's exposure to injury based on one or more exercise results or assessment results.

Athlete Performance Potential rating based on pro athlete normative data for one or more exercise results or assessment results.

During training plans, the system's artificial intelligence uses machine learning to automatically generate next session protocol, which is a progression, regression, or equivalent difficulty of the protocol performed last.

The inventions include computer readable medium containing artificial intelligence for the purpose of exercise prescription to improve overall health, rehabilitation outcomes, or functional performance by using population data and/or personal data collected by a wearable device.

In embodiments, personal data including daily activity, steps, heart rate, ground contact time, foot pressure, gait, cadence, pronation, supination is used to provide patient specific exercise recommendations.

Artificial intelligence analyzes personal data and suggests training routine recommendations. The system's artificial intelligence uses machine learning based on user results, progress, and database data to automatically generate next session protocol, which is a progression, regression, or equivalent difficulty of the protocol performed last based on personal data.

The inventions include a computer readable medium for prescribing physical training routines that improve a user's overall health and functional performance which are improved through routines targeting gait, speed, balance, mobility, motor control, strength, stability, coordination, proprioception, reaction, neurocognitive reaction.

In embodiments, the user can choose between alternative augmented sensor layouts, such as large or small virtual reality sensor boards.

In embodiments, a multi-location database functionality is provided. The multi-location database functionality can be operated through an Admin Overview screen or screens. In embodiments, computer readable medium comprises location based performance and rehabilitation device data. Device data can be filtered in many ways including, but not limited to, a physical location's aggregate data, a regional area's aggregate data. Device data can be further filtered by athlete or patient injury, procedure, affected side, number of athletes/patients, total results, athlete/patient improvement, gender, age, sport, activity level. With filters or no filters applied, database ranks locations by worst, best, or average athlete/patient improvement. Artificial intelligence and machine learning are used to recommend exercises and protocol progressions to lower performing locations based on higher performing locations.

In embodiments, the system includes an algorithm reflecting real-time performance comparison during an exercise. A progress bar is displayed at the bottom of the screen which compares user progress to a set metric. The Progress bar can reflect the user's progress during the exercise compared to the user's worst result, average result, or best result. Progress bar can also be set to reflect a user's progress versus a worst result, average result, or best result of a population, i.e. facility or location, region, country, gender, age, sport, position, injury, procedure, degenerative disease, or any other filters to accurately compare the user to a relevant population.

Progress bar function initiates from the middle of the screen. Progress bar will turn red and increase in length to the left if the user is falling behind the set comparison. Progress bar will turn green and increase in length to the right if the user well ahead of the set comparison. Progress bar is not displayed if the user is on pace to match the set comparison. The system can incorporate an algorithm reflecting real-time symmetry performance during an exercise (FIG. 29). Progress bar is displayed at the bottom of the screen which compares the user's right and left leg performance during an exercise. Progress bar reflects performance based on ground contact times, foot pressure, cadence, impulse, impact force, reaction times. Progress bar can reflect an average of the performance time or the last time recorded. Progress bar scale is calculated by using the standard deviation of the user's symmetry performance history for that exercise. A progress bar function initiates from the middle of the screen. A progress bar reflects symmetry performance by displaying a red bar to the right or left which communicates to the user whether their right or left side is underperforming.

In embodiments, the system provides real-time feedback that reinforces training with the head up, not looking down, and focusing on the real-time feedback which makes training relative to sports and other activities and increases the demands on the nervous system. Real-time feedback capabilities are displayed on the exercise screens.

In embodiments, the tablet App is programmed to train speed, quickness, strength, stability, reaction, coordination, proprioception, mobility, and balance.

The foregoing and other objects, features, aspects and advantages of the invention will become more apparent from the following detailed description of the invention when considered in conjunction with the accompanying drawings.

SUMMARY OF THE DRAWINGS

FIG. 9 shows an embodiment of a screen for tracking athletes or patients for use in the system.

FIG. 17 shows an embodiment of a screen for a workout function for use in the system.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

The system 1000 of the invention improves upon the original QUICK BOARD® system described U.S. Patent Application No. 2013/0224708A1 (Martin), which is incorporated by reference in its entirety. A key feature of the original QUICK BOARD® system is the use of a sensor board to track the performance of an athlete or patient while carrying out physical test routines. The present invention improves upon the original QUICK BOARD® system in various ways. In one embodiment, improvements include substitution of a wearable device 100 or a camera system for the foot sensor pad, along with various software routines for mimicking the performance of a QUICK BOARD® sensor board on a display panel, such as an iPad. This opens up numerous possibilities for use of the system 1000. Rather than being tied to a physical sensor board, as in the prior QUICK BOARD® system, the system 1000 can be set up and used in virtually any setting. The system 1000 incorporates a conventional display panel 10, which will typically be a computer tablet device 11, such as an iPhone® or iPad®. The software 1100 of the system 1000 performs various functions, as described herein.

Figure 1:
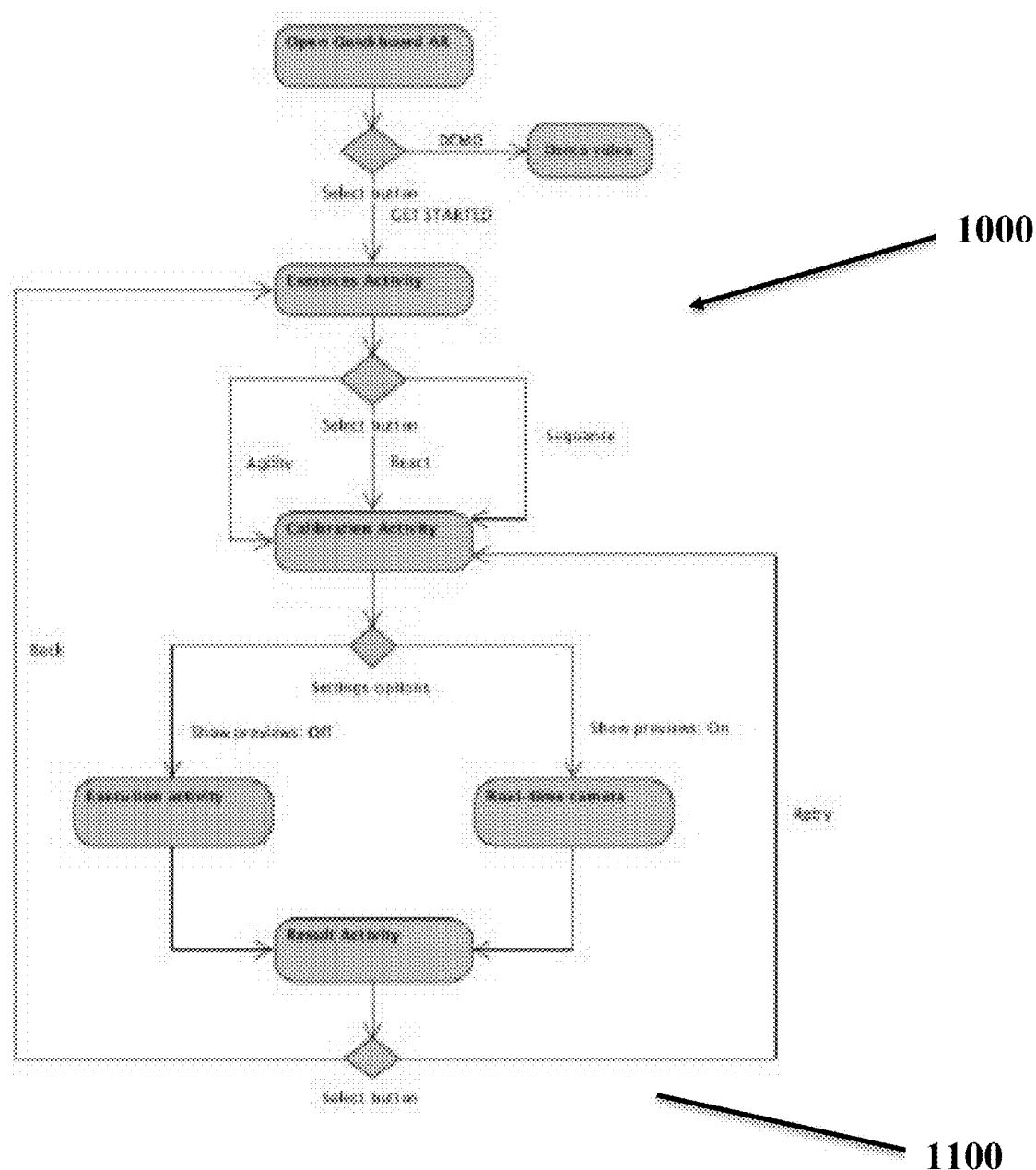
FIG. 1 is a flow chart of an embodiment of the main flow and functions of the system.

FIG. 1 shows a flow chart of the main flow and functions of the system 1000. Using augmented reality combined with video processing algorithms, the system 1000 provides an ideal solution for training. The software 1100 for the system 1000 may be provided as an application 1101. The application 1101 may be in a mobile operating system, such as the iOS or Android operating systems. The application 1101 allows users to perform exercises, such as: Count, React, Sequence, Agility, and Vertical as described below.

The algorithms used for video processing are of two types: (1) Tracking-learning-detection, which is used for tracking user's shoes; and (2) Background change, which is used for detecting presence of shoes on sensors area.

The application 1101 consists of four main screens: Settings, Exercises, Profiles, and Workouts/Protocols. The application 1101 also includes some secondary screens.

On the Exercises screen, the user can select desired exercises to start the training. Exercises are categorized by training goals that may include agility, speed, quickness, reaction, neurocognitive reaction, stability, coordination, strength, proprioception, symmetry, mobility, balance, gait, motor control, and vertical jump. On the Settings screen, the user can select response mode from among: (1) Sensor Board with Bluetooth; (2) AR Board: Follow Shoes or Detect Shoes as the algorithm type used for shoe detection; or (3) Touch Screen: Users can perform exercises by directly touching the device screen.

The system can include and operate using higher level components, such as off-site processors, off-site databases, and the like. System higher level components can be cloud-based and linked via the Internet or other wireless connections.

Calibration

Figure 2:
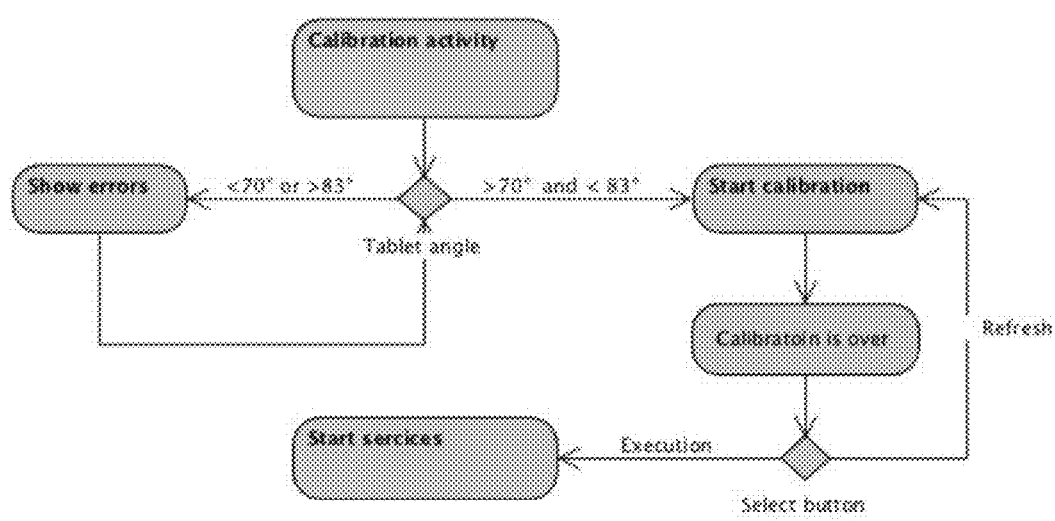
FIG. 2 is flow chart showing an embodiment of flow and function of a Calibration stage of the application

FIG. 2 shows the flow and function of a Calibration stage of the application 1101. Calibration activity is an important step for processing algorithms, requiring some technical positioning of the tablet 11. For example, when using a 12.9 inch tablet 11, the following are recommended: the tablet should be at a height of 63 inches; the tablet angle is between 80 and 83 degrees. When using a 9.7 inch or 10.9 inch tablet, the following are recommended: the tablet should be at a height of 63 inches; the tablet angle is between 70 and 73 degrees. A basic image is saved in the calibration step. The basic image is used in processing algorithm background change, as described below.

Video Processing

Figure 3:
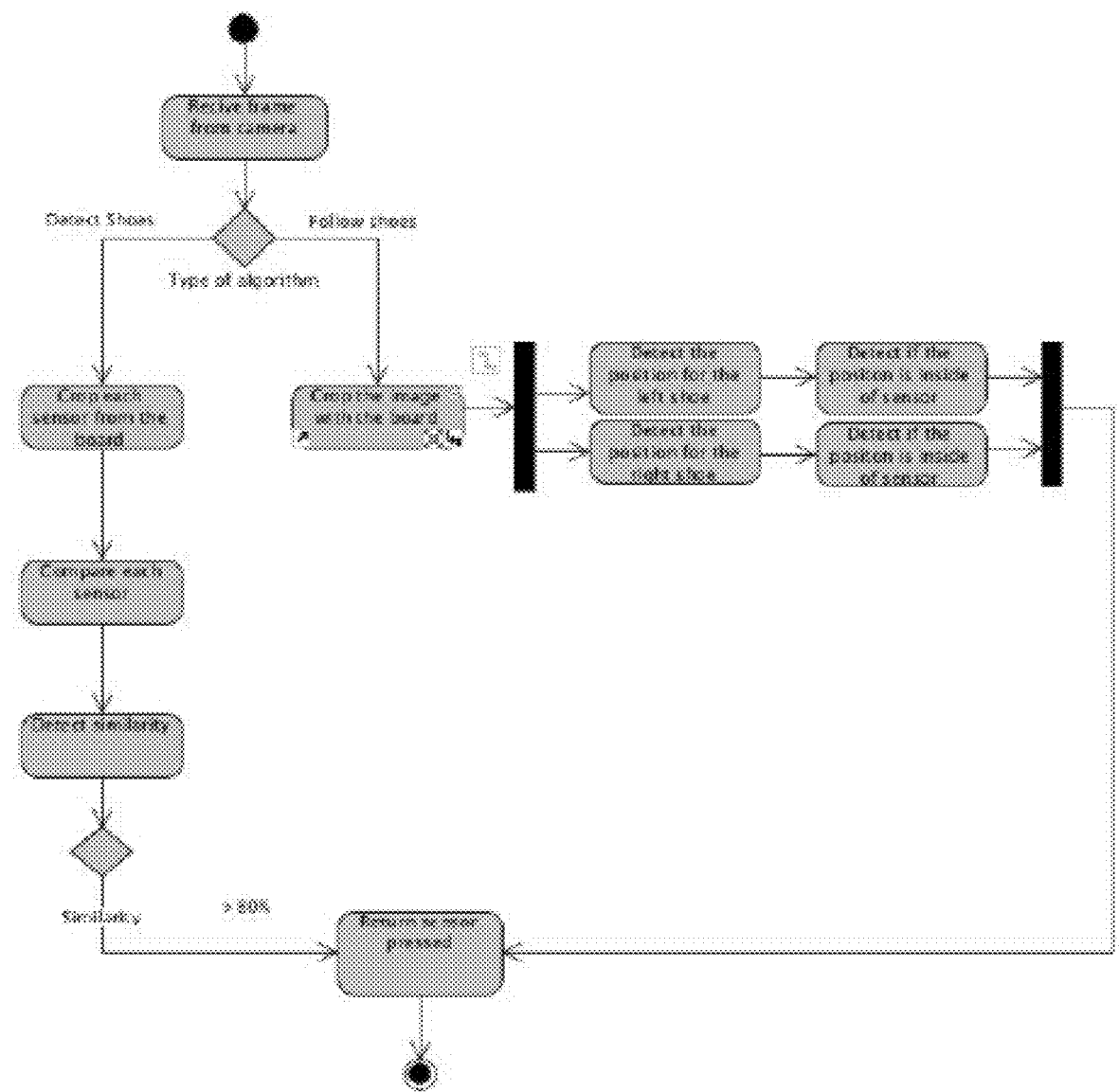
FIG. 3 is a flow chart of an embodiment of a video processing routine.

FIG. 3 is a flow chart of an embodiment of a video processing routine. The algorithms used for video processing are of two types: (1) Tracking-learning-detection, which is used for tracking the user's shoes; and (2) background change, which is used for detecting the presence of shoes on the sensor area.

In the tracking-learning-detection step, two images, one of the left shoe and one of the right shoe, are saved when the exercise begins.

The exercise board of the system 1000 includes five sensors, which will be identified as sensor 1, sensor 2, sensor 3, sensor 4, and sensor 5. The exercise board is saved in four different images: Image 1 contains the sensors 1 and 4; Image 2 contains the sensors 1, 3 and 4; Image 3 contains the sensors 2 and 5; Image 4 contains the sensors 2, 3 and 5.

The tracking-learning-detection algorithm matches the basic images of the shoes in each frame with the images received from the camera. Based on the data received from the matching, another verification is applied using statistical models (correlation) in order to get a numeric parameter that will express how well the two images match with each other.

The first detected shoe is the left one. Depending on its coordinates from the algorithm, the system 1000 decides on which image the right foot will be detected. After detecting the coordinates for the left and the right shoe, the system 1000 determines if they are inside the sensor radius. The background change algorithm is used for detecting the presence of shoes on the sensors area. In order to detect the presence of a shoe on the sensors on the board, the system 1000 uses the difference between the basic image (from the calibration step) and each frame received from the camera.

Augmented Reality (AR) Using Wearable Devices

Figure 4A:
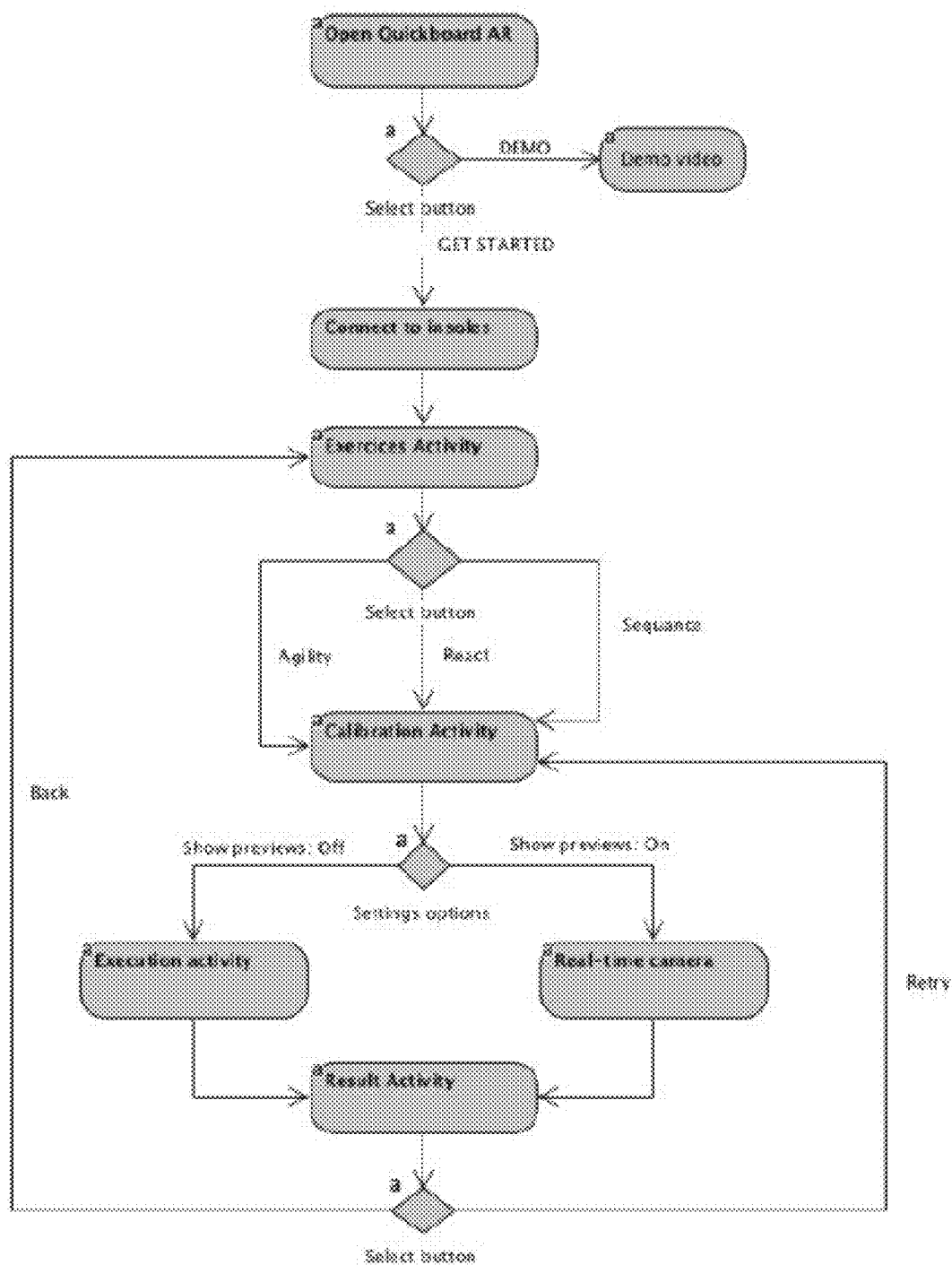
FIGS. 4A and 4B provide a block diagram of an embodiment of the system configured for use with a wearable device.
Figure 4B:
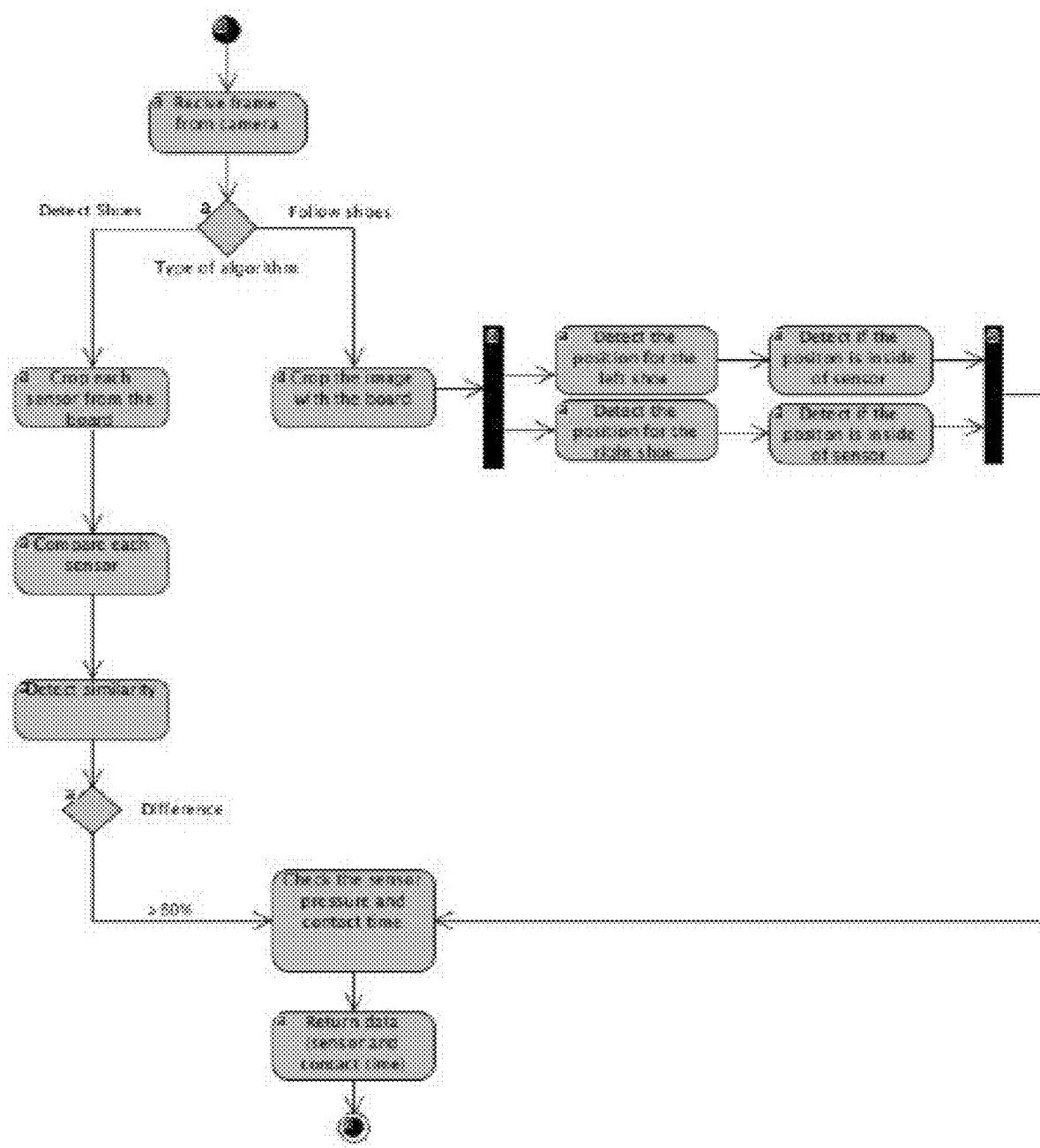

FIGS. 4A and 4B show a block diagram of the system 1000 configured for use with a wearable device 100. For integration with the wearable device 100, the flow shown above is used. The wearable devices 100 are used to validate that the shoe is in contact with the ground and to measure the contact time in sensor areas 1-5. Integration with insoles 100 allows the system 1000 to analyze more user data, such as: Gait, Cadence; Foot strike; Pressure; Impulse; Impact force; Contact time; Air time; Pronation; Supination.

AR iPad system may have two components: Lite Version and Extended Version. The Lite Version carries out exercises without any hardware, other than a tablet device such as an iPad. The Extended version includes connection to external hardware ie insole, pressure sensors, smart shoes etc.

Lite Version Setup: First, an athlete/patient is entering into calibration mode. By using the iPad camera, the system detects the shoes and helps the user setup the place of a virtual board. After calibration, the user will be able to test some drills on a training screen. The user will see his legs on the screen. Once the user is used to the position and distances, he or she can start doing drills with AR. Lite Version exercises: There is a list of exercises specific for AR. Users can do Sequence Drills, Count Drills, Agility Drills, Vertical Drills and React Drills. Users can perform exercises for improving agility, speed, quickness, reaction, neurocognitive reaction, stability, coordination, strength, proprioception, symmetry, mobility, balance, gait, motor control, vertical jump (power).

The Agility Drill functions differently than the Count, Sequence, React, and Vertical drills. For Count, Sequence, React, and Vertical drills, the user stays in the camera view with augmented sensor areas displayed around them.

For the Agility Drill, a single sensor location is displayed in the middle of the screen which marks the area where a user should stand. During an Agility Drill, an arrow appears on the screen, then a user will leave the sensor location within the camera's view to move to a predetermined location outside of the camera view, which starts a timer.

Once the user has moved to the predetermined location, outside of the camera view, identified by cones, tape, and other types of physical markers, and returns to the sensor location within the camera's view, the timer stops. At this point, the user will wait for the next arrow to appear then the timing process will repeat. Repeated start-stop intervals provide performance data for assessing agility. Agility Drill with Augmented Reality provides objective movement times to the user and communicates whether they are improving their agility performance.

Extended Version. The initial setup is the same as the Lite version. After the initial setup, users can connect with external hardware, such as a wearable device 100, and cover all of the exercises and obtain additional user metrics with the external hardware including Cadence; Foot strike; Pressure; Impulse; Impact force; Contact time; Air time; Pronation; Supination.

Figure 38:
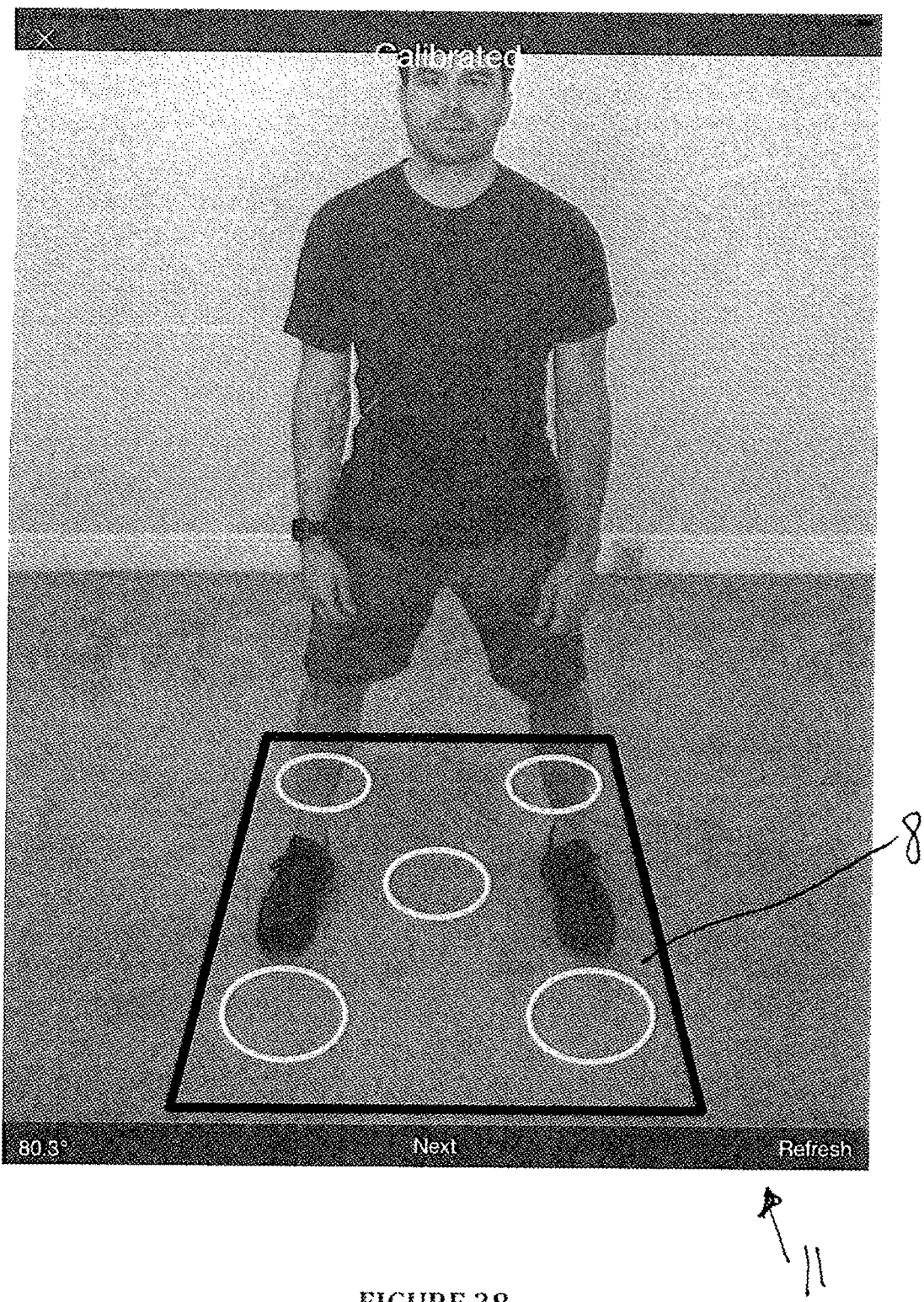
FIG. 38 is a view of a screen showing an option in which a user sees an image of himself or herself superimposed on an image of a virtual sensor board during use of the system to perform exercises.

FIG. 38 is a view of a screen showing an option in which a user sees an image of himself or herself superimposed on an image of a virtual sensor board 8 during use of the system to perform exercises. Alternatively, the user can elect to see the execution screen which is a visual representation of the augmented areas, without the user's image on the screen (see FIG. 29), in the manner of prior embodiments of the system.

Wearable

"Wearable device" or "wearable" as used in this application means a sensor device that is worn by the user that receives and transmits information to and from the system. The wearable device 100 will typically be worn on the foot or shoe of the user. The wearable device 100 may take various forms, provided that it signals movement and sufficiently interacts with the system 1000 to create an augmented reality effect. The wearable device 100 is configured to withstand the rigors of repeated use in the exercises described herein, yet is ideally modestly sized and profiled so as not to impede the motion of the user or to cause fatigue, discomfort and other negative effects of use. For example, the wearable 100 can be an insole that is worn inside of the shoe of a user. In other embodiments, the wearable can attach to or clip on to the shoe of the user, such as to the laces of the shoe. In other embodiments, the wearable device 100 can be an insert that fits inside the user's shoes, such as under the insole of a shoe. In some embodiments, the wearable is used to track motion of the arms or hands. Static and dynamic foot pressure received from the wearable device 100 can be used in the system 1000. Static and dynamic foot pressure received from the wearable device 100 can be used for user authentication not associated with gait. U.S. Pat. No. 9,357,947 B2 (deGreef et al.), assigned to Bend Tech, LLC, which is incorporated herein by reference in its entirety, provides an example of a wearable device 100 that can be used in the system 1000 of the invention.

Figure 36:
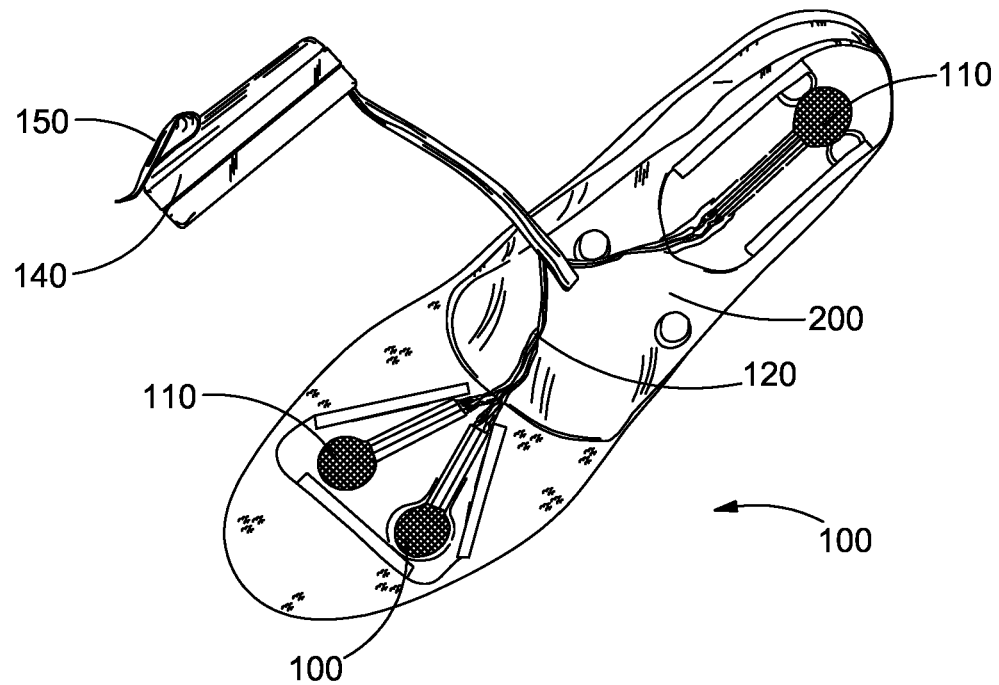
FIG. 36 is an embodiment of a wearable device configured for use with the system.
Figure 37:
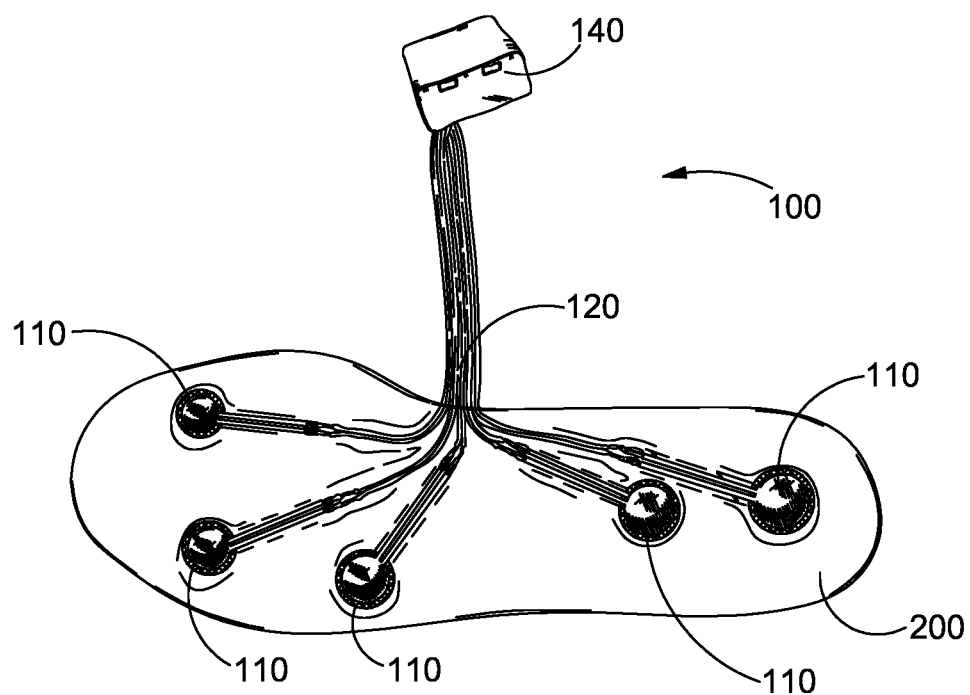
FIG. 37 is a an embodiment of a wearable device configured for use with the system.

A wearable device 100 is provided for each shoe of a user. The wearable device 100 can be configured to clip to the shoes of the user, collect user data during exercises, and transmit the data to the pad device. In the embodiments shown in FIGS. 36 and 37, the wearable device 100 is a sub-insole device that sticks to the bottom of an insole 200 of each shoe of a user. The wearable may include one or a plurality of sensors 110 that are distributed on the bottom of a shoe insole 200 so as to detect pressure and touches at selected parts of the foot. The shoe insole can be an insertable orthotic. The sensors are attached to the bottom of the insole, such as by tape or an adhesive. In embodiments, the plurality of sensors includes one, two, three, four or five sensors. The individual sensors 110 are configured to sense pressure. The sensors 110 can be pressure sensors, bend sensors, and the like. In embodiments, the sensors 110 are electrically coupled by a bridge 120 to a component housing 140. The component housing 140 encloses and protects a collection of wearable operative components that are configured to collect user data and transmit the data to the system during use of the exercise programs. The operative components in the housing include a circuit board having a processor, a battery, and a transmitter. The operative components can include orientation components such as an accelerometer; an accelerometer and gyroscope; or an accelerometer, gyroscope and magnetometer. Adding orientation components to the circuit board gives additional data points in addition to the data collected from the sensors and camera, which enables additional capabilities.

The operative components sync user data to the display pad, which in turn syncs the data to the system. In embodiments, the operative components transmit the data via blue tooth low energy (BTLE). The battery may be chargeable, such as through a conventional electrical outlet, by wireless charging, and the like.

The bridge 120 between the sensors and the component housing can be an elongated cable, such as a flat cable. A shoe attachment means 150 can be provided on the component housing, such as a clip 150 or other mechanism for selectively and removably attaching the component housing to the shoe of a user. In embodiments, the attachment means can include a pouch that attaches to the shoe and is sized to securely receive the component housing.

Training Plan

In some embodiments, the wearable device 100 is worn even when not performing system exercises. During use, the system tracks daily activity, accumulating data that can be used to provide patient specific exercise recommendations. The system can use AI to analyze the data and make exercise recommendations. For example, the system 1000 can track gait and foot pressures in the system 1000 software and suggest exercises based on that information. The wearable solutions make the system 1000 methodology stronger because in addition to ratings assessments, the system 1000 obtains additional data points to create training or rehab suggestions. The training plan can be configured to improve gait and balance, manage disease (Parkinson's, Alzheimer's, ALS, and other neurodegenerative diseases), and improve performance in areas such as agility, speed, quickness, reaction, neurocognitive reaction, stability, coordination, strength, proprioception, symmetry, mobility, balance, gait, motor control, vertical jump (power).

For rehabilitation, the system 1000 tracks and treats patients in the clinic, between clinic visits, and remotely for telerehab applications. Between clinic visits, the software 1100 tracks the patient's activity and prescribes exercises. In embodiments, the data is analyzed by Artificial Intelligence (AI) and machine learning to create a rehabilitation plan for their next home session or clinic visit. In embodiments, the System 1000 software and insole can be used to track exercises at home for telemedicine applications.

Methods of using the system 1000 will now be described with reference to specific exemplary individual screens. It will be appreciated that the actual screen appearances and flow of processes may differ with departing from the spirit and scope of the invention.

The System 1000 system is used for sport performance training, and physical therapy. Training and Rehabilitation progress is objectively tracked. Physical therapists and performance professionals can set up the app to customize patient or athlete specific protocols, save results to patient or athlete profiles, and track progress. The most important capability is providing real-time feedback that reinforces training with the head up, not looking down, and focusing on the real-time feedback which makes training relative to sports and other activities and increases the demands on the nervous system.

In embodiments, the "sensor board" is a virtual sensor board 8. The System 1000 sensor board connects to a tablet, such as an iPad®. The tablet App is programmed to train speed, quickness, strength, stability, reaction, coordination, proprioception, mobility, and balance. The system 1000 software is fully customizable to target speed, quickness, strength, stability, reaction, coordination, proprioception, mobility, and balance.

Testing

The system can be configured for use in testing. Examples of testing include: Track athlete's speed and monitor for over-training; quickly highlight asymmetry resulting from dominance or previous injury; capture baseline data for critical discharge or return to play decisions.

The System 1000 identifies asymmetry due to dominance or injury.

Highly reliable and time efficient single leg hop testing
Bilateral reaction
speed
quickness
coordination
strength
stability
mobility
balance
Proprioception The system 1000 assists performance and rehabilitation staffs develop athlete specific workout programs.

The system 1000 is scientifically proven for testing quickness and reaction time.

Research study concluded NBA All-Stars reacted faster than veterans and rookies (3 teams).

The system 1000 Bilateral React Drill is used to test athletes for overtraining.

University of Louisville overtraining study found The system 1000 reaction test was more sensitive to overtraining than vertical jump.

Physical therapists and athletic trainers use the system 1000's baseline data to make crucial return to play decisions.

Training

The system 1000 reliably trains and is scientifically proven to increase agility, quickness, and reaction.

Correlates to other components of an explosive athlete, i.e. vertical jump and short distance sprints.

It is important to train quickness as it can improve outcomes of other explosive movements.

The system 1000 is the only device that provides the capability and method to test and train lower extremity coordination, which can reduce athlete exposure to injuries.

The system 1000 is the only device that tests and trains proprioception by providing real-time feedback on the tablet so athletes do not look down at their feet.

Research has consistently proven that instant feedback results in significant performance increases. An important capability of the system is providing real-time feedback that reinforces training with the user's head up, not looking down, and focusing on the real-time feedback, which makes training relative to sports and other activities and increases the demands on the nervous system.

Rehabilitation

Use of the system 1000 rehabilitates both neurologically and physically. The system 1000 takes the guesswork out of return-to-play decisions with pre versus post injury drill comparisons. The system 1000 restores confidence with objective improvements. The system 1000 tracks daily/weekly progress and provides reports which convey progress to the patient and other therapists. The system 1000's real-time feedback and objective data result in a goal-oriented rehab. The system 1000 is implemented in every phase of weight bearing rehab for a wide range of patient populations. The system 1000's real-time feedback enhances the proprioceptive benefit of exercises by performing tasks with the head up in order to address neuroplasticity and fully restore pre-injury communication. The system 1000 collects baseline data points needed for pre versus post injury comparisons. If pre-injury data is not available, healthy versus injured side can easily be compared.

Tablet App

The system 1000 can provided in the form of a tablet application. The app is configured to track an athlete's speed and monitor for over-training. Features include: quickly highlight asymmetry resulting from dominance or previous injury; control one or more tablets from a phone or tablet with the system 1000 app; facilities with multiple systems have the option to select and start exercises with a single tablet to keep clients moving efficiently; change the list order of exercises and categories on Include Exercises and in an Athlete profile; record a user performing a system 1000 exercise from the tablet with the system 1000 app and pair the video with the results; optional audible sound when a sensor is pressed in all exercises (distinguishable from the error beep); auto-playlist takes users through exercises and saves data to their profile, displays demo videos during rest time, and provides previous, average or best result during rest time; paired Exercises identify user deficits; isolate reaction active sensor areas; workouts/Protocols (automated or manual); send facility, team, user progress reports; real-time feedback meter/gauge comparing to the user's previous, average or best performance; the gauge can compare to average or best for facility, team, sport, position, age, gender, activity level, athlete level, disease, injury (e.g. compare to average or best of any information collected by the system 1000); contact and reaction times displayed in real-time over sensor areas on the tablet; augmented Reality for upper and lower body (used with or without additional hardware); Rating Generator based on upper and lower body user data the system 1000 collects over time; ratings including but not limited to: Agility Rating, Symmetry Rating, Return to Play Rating, Reaction Rating to monitor nervous system function, Injury Exposure Rating, Athlete Performance Potential rating (identifies high performing athletes, e.g. All-Stars, based on athlete data in the system 1000 database); rating based on injury, procedure, or disease, e.g. ankle sprain, ACL sprain, Total Joint Replacement, Parkinson's, Alzheimer's, etc.; Artificial Intelligence (AI) provides exercises/protocol suggestions based on rating received where the user needs to improve; AI will suggest protocols based on user profile information only, e.g. age, gender, sport, position, athlete level, injury added to profile, disease, activity level, height, weight (this handles automatically sending protocols based on user demographics without performing a rating assessment); AI automatically progresses users through protocols based on time or results; AI will modify protocols based on exercise results and progress, ie they may be doing well and need more challenging exercises; software integrates with any hardware device, e.g. board with multiple sensors, insole, shoe, sock, removable device that goes on or in shoe or foot, that tracks touches, pressure, force, contact time, airtime, speed, etc.; dynamic react adjusts speed of dots appearing or disappearing based on user's reaction time during the exercise; import data from other devices, eg Apple Watch, FitBit, Sleep, Activity, etc.; or video streaming, remote monitoring the system 1000 technology for telemedicine or coaching purposes.

Healthcare Version

The healthcare version of the system 1000 is different from the performance version. For HIPAA compliance, patients cannot see other patient names in the app. In the healthcare version, all patient names are hidden and limits application accessibility. The system 1000 provides patients with the option of quickly pulling up their own profile. A process for a patient to quickly pull up their profile is created.

Web App

A web-based version of the system 1000 provides customers who have more than one location with an administrative dashboard that shows overviews from the various locations. This allows for identification and analysis of the performance of multiple locations. A web-based embodiment can include various functions, such as: make data comparisons displayed on dashboard chart modifiable so administrator's can control the location comparisons based on the fields filled out in a profile, eg age best, age average, gender best, gender average, injury average, injury best etc.; athletes/patients comparison; leaderboards; Artificial Intelligence (AI) for generating workouts or protocols based on results; automatically import sleep and activity from fitness trackers (e.g. Apple Watch®, Fitbit®, Garmin®, Sleep Number®, Beddit®, etc.) so facilities can track client activity and provide correlations with system 1000 data along with other data points; Rating Generator based on upper and lower body user data the system collects over time (including but not limited to: Agility Rating, Symmetry Rating, Return to Play Rating, Reaction Rating to monitor nervous system function, Injury Exposure Rating, Athlete Performance Potential rating (identifies high performing athletes, e.g. All-Stars, based on athlete data in the system 1000 database)); rating based on injury, procedure, or disease, e.g. ankle sprain, ACL sprain, Total Joint Replacement, Parkinson's, Alzheimer's, etc; Artificial Intelligence (AI) provides exercises/protocol suggestions based on rating received where the user needs to improve; AI suggests protocols based on user profile information only, e.g. age, gender, sport, position, athlete level, injury added to profile, disease, activity level, height, weight (this handles automatically sending protocols based on user demographics without performing a rating assessment); add/send exercises with demo videos to all or select subscribers; add/send workouts to all or select subscribers; provide users the capability to classify a custom exercise as a testing, training or rehab exercise.

Authorization

Figure 35:
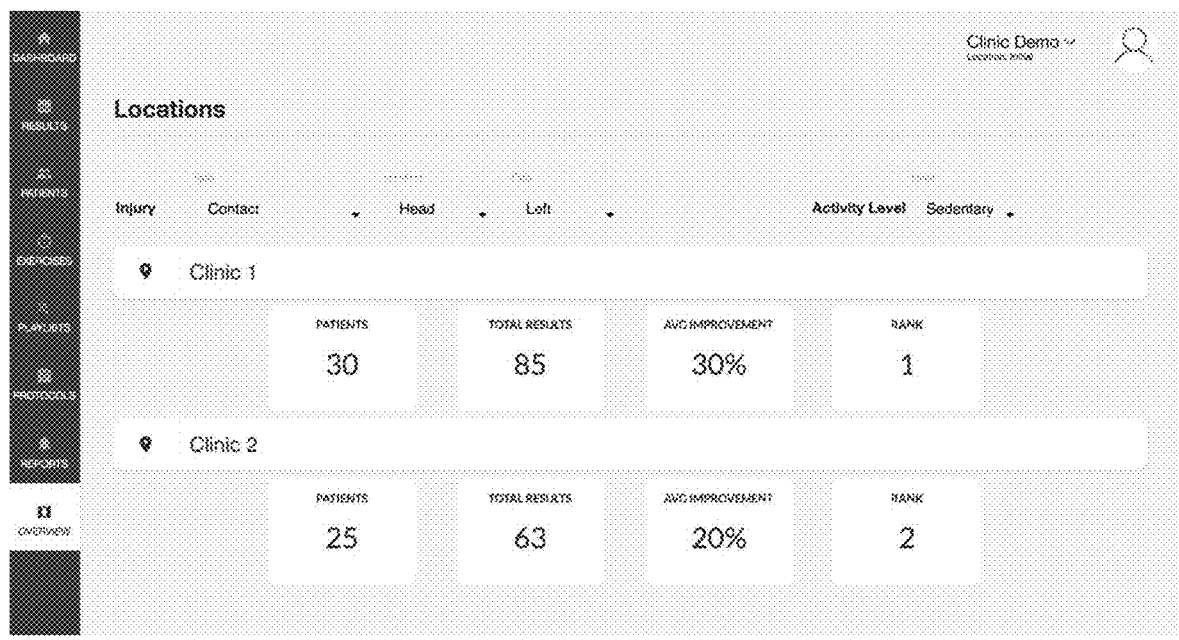
FIG. 35 shows an embodiment of a screen for an administrator overview dashboard for use in the system.

FIG. 35 shows a screen for an administrator overview dashboard. Roles within the app include: Administrator; Location Administrator; and Athlete/Patient.

Administrator level may include the following functions: access to all the data within the organization; add, edit and delete athletes/patient (an athlete/patient is a person who performs exercises using the system 1000); add, edit and delete injuries to athlete/patient profile; add, edit and delete exercises (an exercise is an activity requiring physical and mental effort, carried out especially to sustain or improve health and fitness using the system 1000 app).

it can add, edit and delete playlists. A playlist is a list of exercises that can be in a selected order.

it can add, edit and delete workouts or protocols. A workout or protocol is a list of playlists.

it can edit or delete results. A result is the outcome of an exercise performed on System 1000.

it can add locations. A location is a sub-organization with athletes/patients, exercises, playlists, workouts, results. Data between locations is not shareable, but location-based analytics will be provided to the admin.

it can add location administrators (trainer/coach/therapist). They can be assigned to one or more locations those having access to the data from those locations.

it can view stats based on the system 1000 usage it can view athlete/patient results.

it can create report rules.

based on the report rules created, it will receive a document displaying the progress of the athletes/patients.

it can edit the organization billing info.

it can edit or delete the organization account.

It can edit the organization address, name, contact phone number, etc.

it can select what athlete profiles, exercises, workouts/protocols sync with each tablet of a location.

it can move athlete/patient profiles, exercises, workouts/protocols and other data between locations.

it will have access to an admin dashboard which displays summarized athlete/patient data by location or region. Filters are provided to sort location or region based data by athlete or patient injury, surgical procedure, affected side, number of athletes/patients, total results, athlete/patient improvement, gender, age, sport, activity level. With or without filters applied, database ranks locations by worst, best, or average athlete/patient improvement. Artificial intelligence and machine learning are used to recommend exercises and protocol progressions to lower performing locations based on higher performing locations.

Location Administrator→will have access to one or multiple locations data within the organization. When created, if the admin gives it the permission to create/edit data (write) than the location administrator:

can add, edit and delete athlete/patient profiles;

can add, edit and delete injuries to athlete/patient profile.

can add, edit and delete exercises can add, edit and delete playlists can add, edit and delete workouts or protocols can select what athlete profiles and exercises sync with each tablet of a location.

can view athlete/patient results.

can create report rules.

based on the report rules created, it will receive a document displaying the progress of the athletes/patients.

can have access to the dashboard for the location(s) where it was assigned.

Location Administrator→if the location adminstrator has only read permission the can only see the data without modifying it.

Athlete/Patient→will have access only to the data associated with his profile.

it can view its results it can view its associated playlists it can view its associated workouts it can view a dashboard with his latest exercises results Exemplary Methods of Use Methods of using the system 1000 will now be described with reference to various exemplary screens for use in the system 1000.

Figure 5:
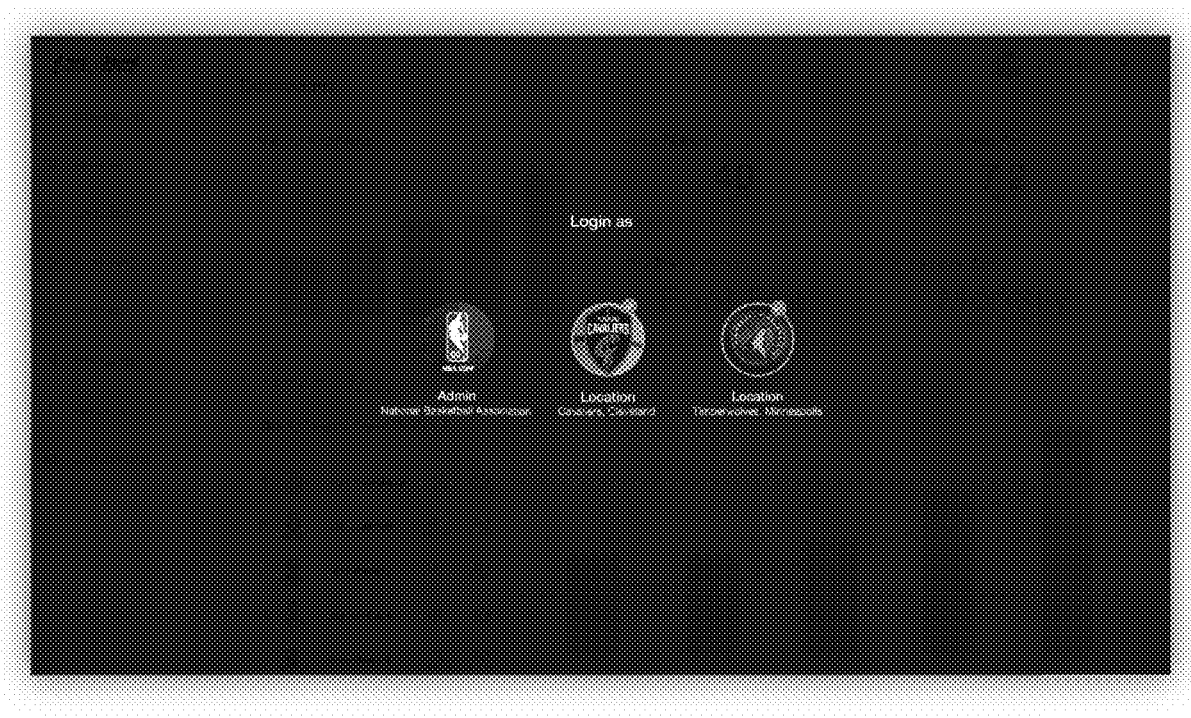
FIG. 5 shows an embodiment of a location screen for use in the system.

FIG. 5 shows an exemplary location screen. A location is a sub-organization with its own athlete/patient profiles, exercises, playlists, workouts, results. Data between locations is not shared, but analytics based on the usage of each location will be provided to the admin. When an account is created, a default location is created. Data can be moved or cloned between locations, e.g., athletes/patient profiles can be moved between location, but exercises are cloned between locations.

Figure 6:
FIG. 6 shows an embodiment of a screen for a dashboard for use in the system.

FIG. 6 shows an exemplary screen for a dashboard. The dashboard screen provides analytics to the administrator/location administrator based on usage of the system 1000 and results of individual athletes/patients.

Figure 7:
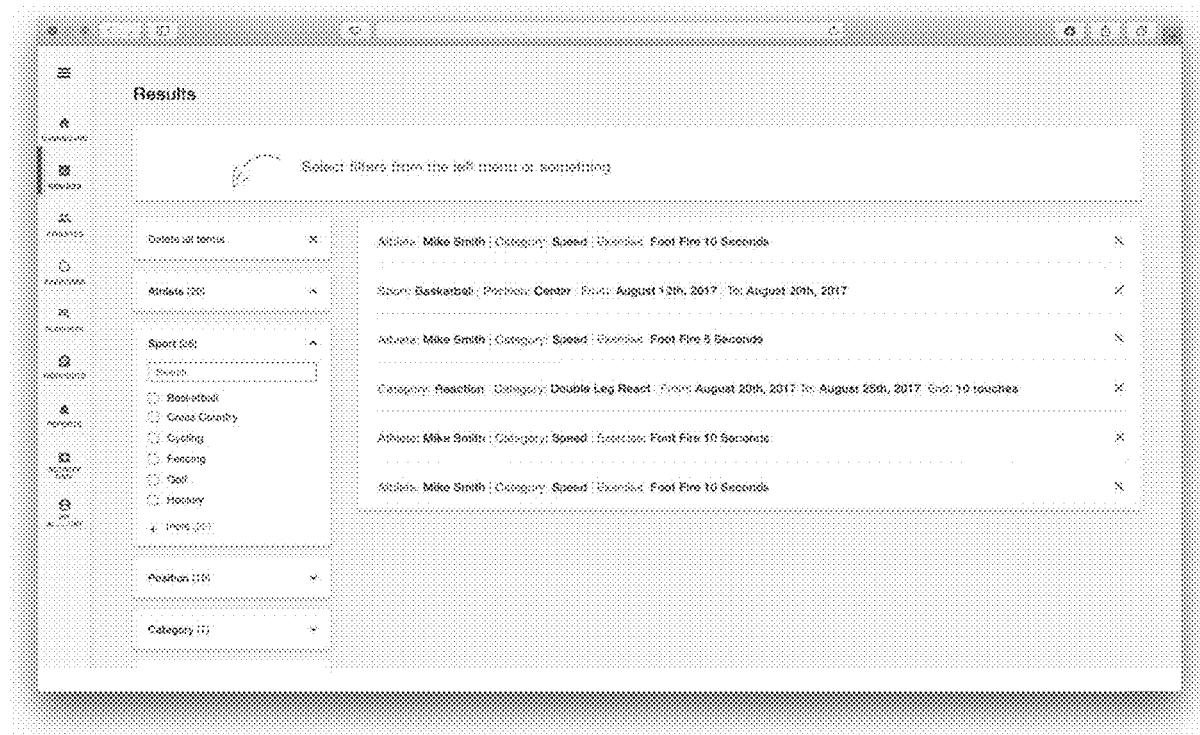
FIG. 7 shows an embodiment of a screen for a results page for use in the system.

FIG. 7 shows an exemplary screen for a results page. The results page displays some generic data of the most recent exercises results for a selected location. The results can be filtered based on data present in the athlete/patient profile or in the exercise settings. If a result is selected than the admin/location administrator can view more in depth data, e.g. average reaction times and contact times by sensor location.

On the results section, a location administrator or admin can delete a result or associate it with another athlete/patient profile. Based on the filters selected an admin/location administrator can generate a report rule.

When the rule is generated, the admin/location administrator must select how often it wants the rule to be executed.

When a report rule is executed, an email with a progress document is sent to the admin and location administrators associated with that location and applied report rules.

Admin or location administrators can opt out from receiving reports that they haven't generated.

Each result will have a rating. Using the rating, the AI can generate exercises, workouts and other protocols to help patient recovers and athletes improve their performance. A "Rating" generator will make it easier to add various ratings based on algorithms. For physical therapy, a rating can include a patient symmetry rating which takes contact times, reaction times and paired exercise results into consideration to come up with a rating based on all of those data points. For sports, ratings can include an Agility rating and a Preparedness rating. The Agility rating is a composite of select exercise results. The system 1000 provides areas where the user can improve with suggested workouts or protocols. The Preparedness rating is displayed after an athlete performs a Double Leg React test. The system 1000 bases the preparedness rating off the standard deviation over the past X number of Double Leg React exercises for that athlete. For example, within 5% correlation, the user gets a green dot, between 5-10% a yellow dot, and greater than 10% a red dot.

Figure 8:
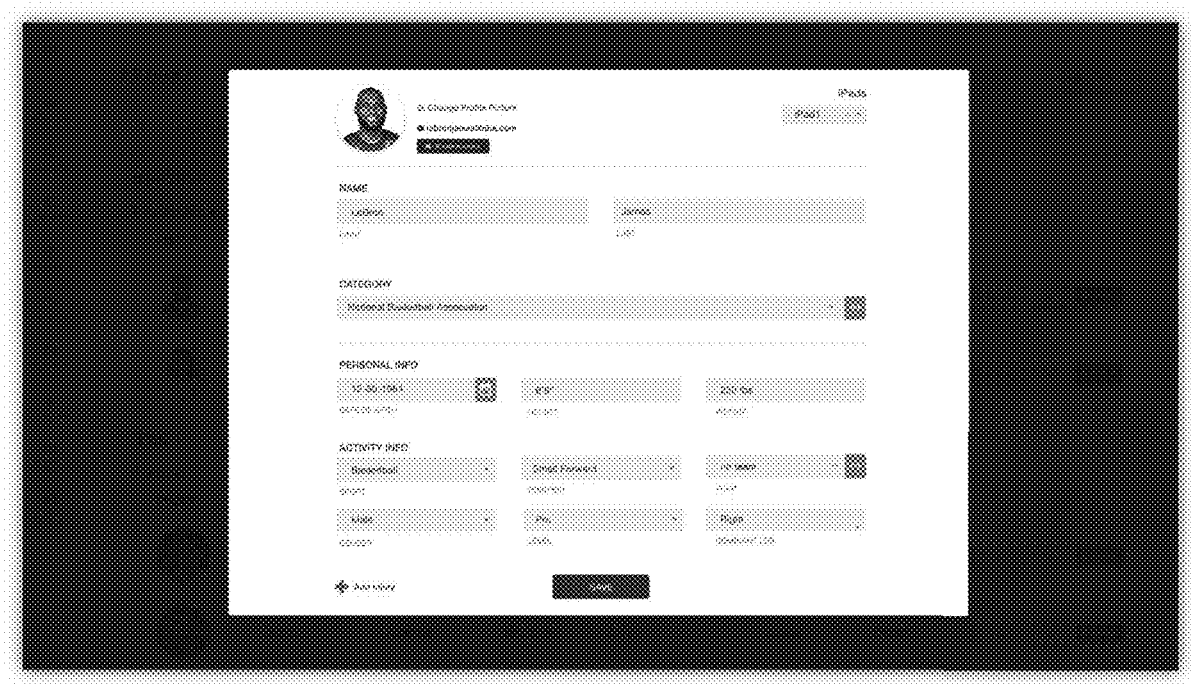
FIG. 8 shows an embodiment of a screen for changing or updating a profile of an athlete or a patient for use in the system.

FIG. 8 shows an exemplary screen for changing or updating a profile of an athlete or patient. The screen can be customized. For example, particular sports can be selected from a drop down menu.

Figure 9:
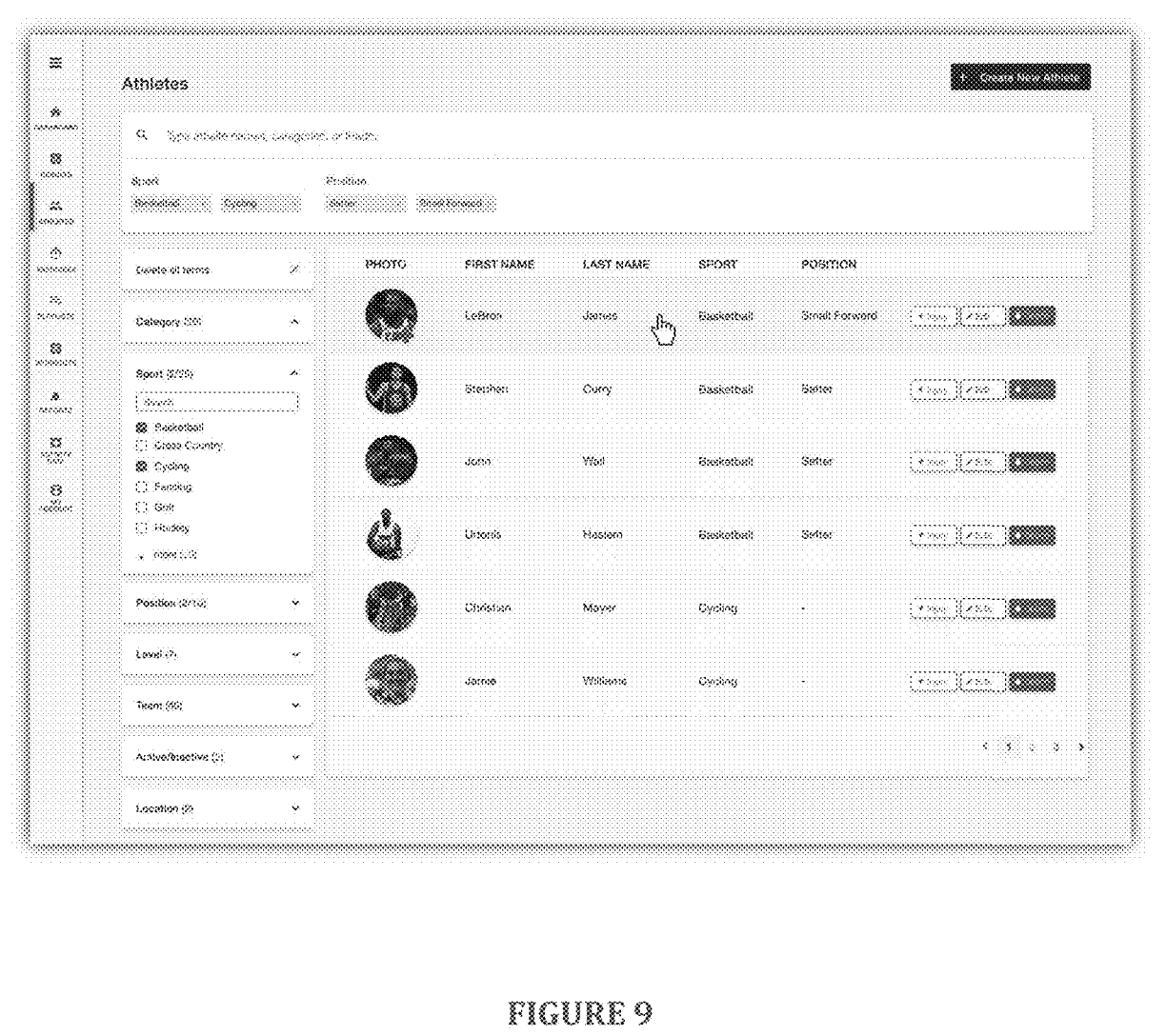

FIG. 9 shows an exemplary screen for tracking athletes or patients. An admin or location administrator who has write privileges can use the athlete/patient screen to: see how many active/inactive athlete/patient profiles are in the location; search for an athlete/patient profile by name; search for an athlete/patient profile by other information present in the profile; add an injury to an athlete/patient profile; add athlete/patient profiles using the following info: full name, date of birth, height, weight, sport, position, category, team; activate or deactivate athlete/patient profiles (e.g. an athlete that has been using the system 1000 app more than four days will be considered active); an admin/location administrator can edit athlete/patient profile details and injuries; if an athlete is injured, his exercise results are marked accordingly. The profile for an athlete contains the athlete's activity history.

Figure 10:
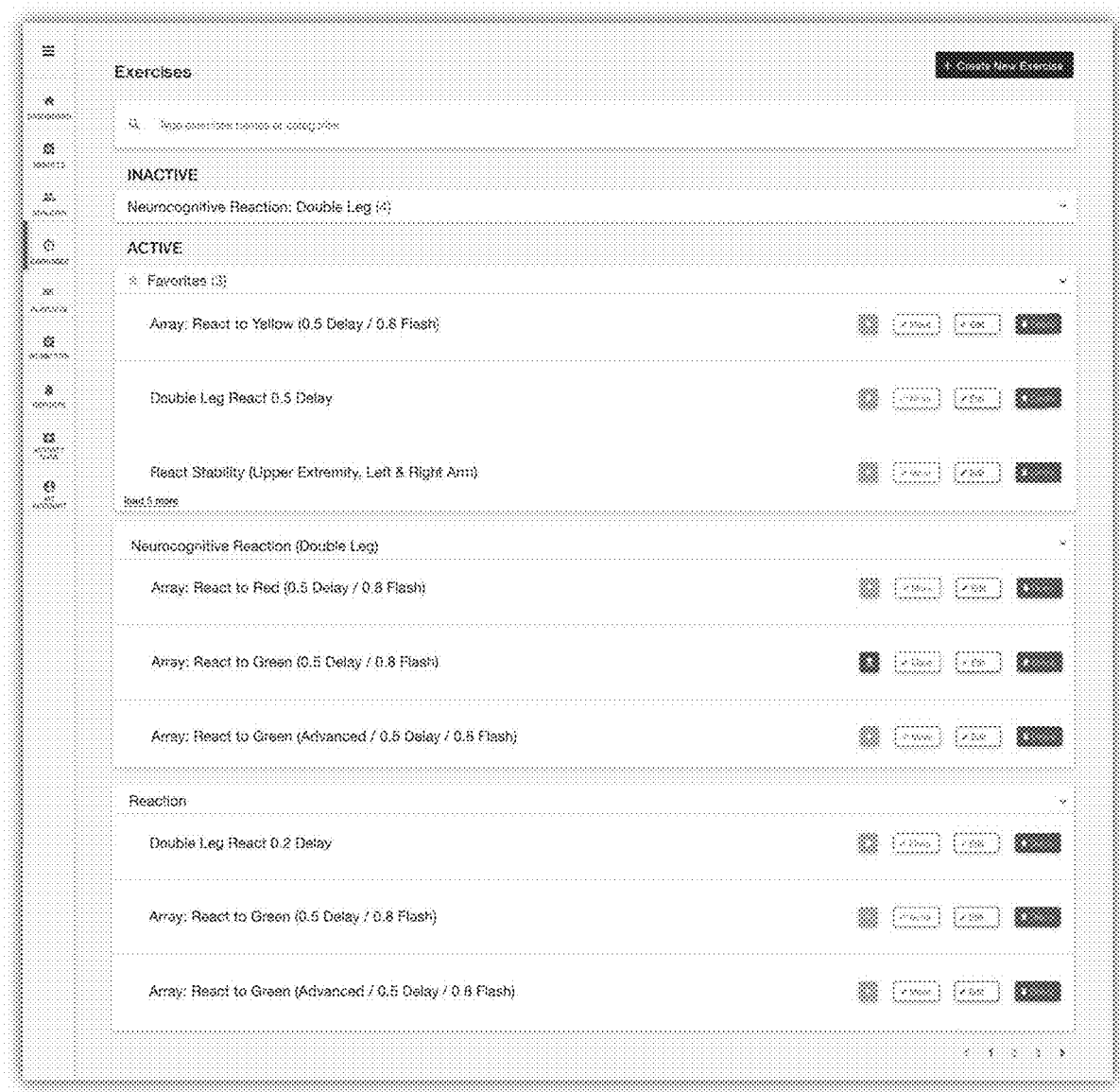
FIG. 10 shows an embodiment of a screen for exercises for use in the system.

FIG. 10 shows an exemplary screen for Exercises. An admin or location administrator with write privileges can create and edit exercises on the Exercise Screen. If a user has only read privileges he can see the exercises, but cannot edit the exercise settings. Exercises are split into the following types: active: get pushed to the iPad if the iPad has no preselected data that should sync with it; inactive: not pushed to the iPad, but might be activated or kept for future reference.

Figure 11:
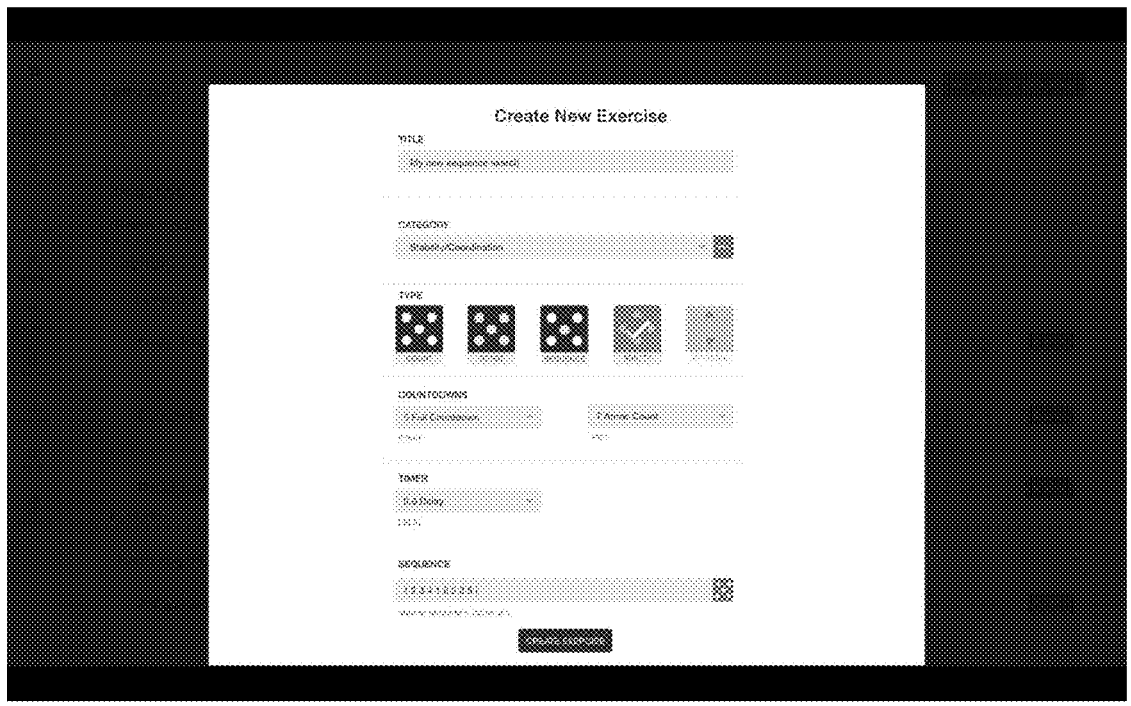
FIG. 11 shows an embodiment of a screen for creating an exercise for use in the system.

FIG. 11 shows an exemplary screen for creating an exercise. In FIG. 11, the location administrator is selecting creation of an agility exercise, but other options may include count, react, sequence, and vertical (jump). An admin/location administrator can use the exercise screen to:
 create a new Exercise
 edit an existing Exercise
 delete an existing Exercise
 view the video of an exercise
 activate/deactivate an exercise
When creating an exercise, a admin/location administrator must:
 select type of the exercise (agility, count, sequence, react, vertical)
 select or create a category for the exercise
 enter the exercise name
 fill out exercise details. E.g. start type (when should the exercise start after a selected or random number of seconds), end type (when should an exercise end, after a selected number of touches or seconds), end value, etc.
 the admin/location administrator has also the option to upload a video demonstrating how the exercise should be performed.
Properties that are common for all exercises types:
 category of the exercises.
 name of the exercise.
 start type: countdown or random start.
 start value: the value of the countdown.
 end type: after number of sensor pressed or seconds expired.
 end value: the value when an exercise should end.
In addition to common properties, each specific type of exercise can have entries for recording details specific for the type of exercise.

Figure 12:
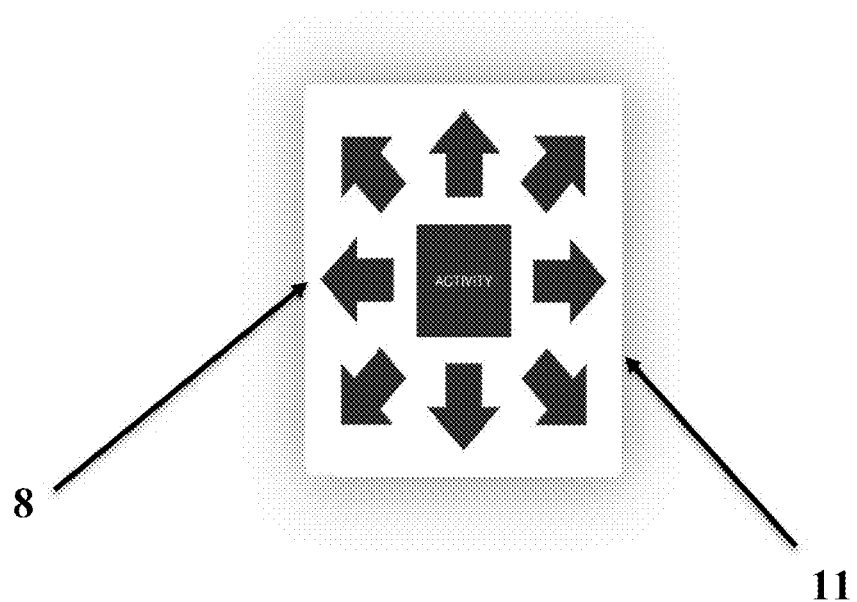
FIG. 12 shows an embodiment of a screen for an agility drill for use in the system.

FIG. 12 shows an exemplary screen for an agility exercise. Features of the agility exercise include:
 delay: the delay between displaying actions.
 sequence type: sequence or random.
 if sequence is selected, then the admin/location administrator should select the sequence in which the actions should be displayed.
FIG. 12 shows the sequence represented by arrows changing every 45 degrees, and representing the position where the athlete should move. In the square shown in the middle, the activity will be written, e.g., jump or push up. Each sequence can be represented either as numbers from 0 (the activity) to 9, 1 being the arrow facing up, and 8, the arrow at −45 degrees.

Figure 13:
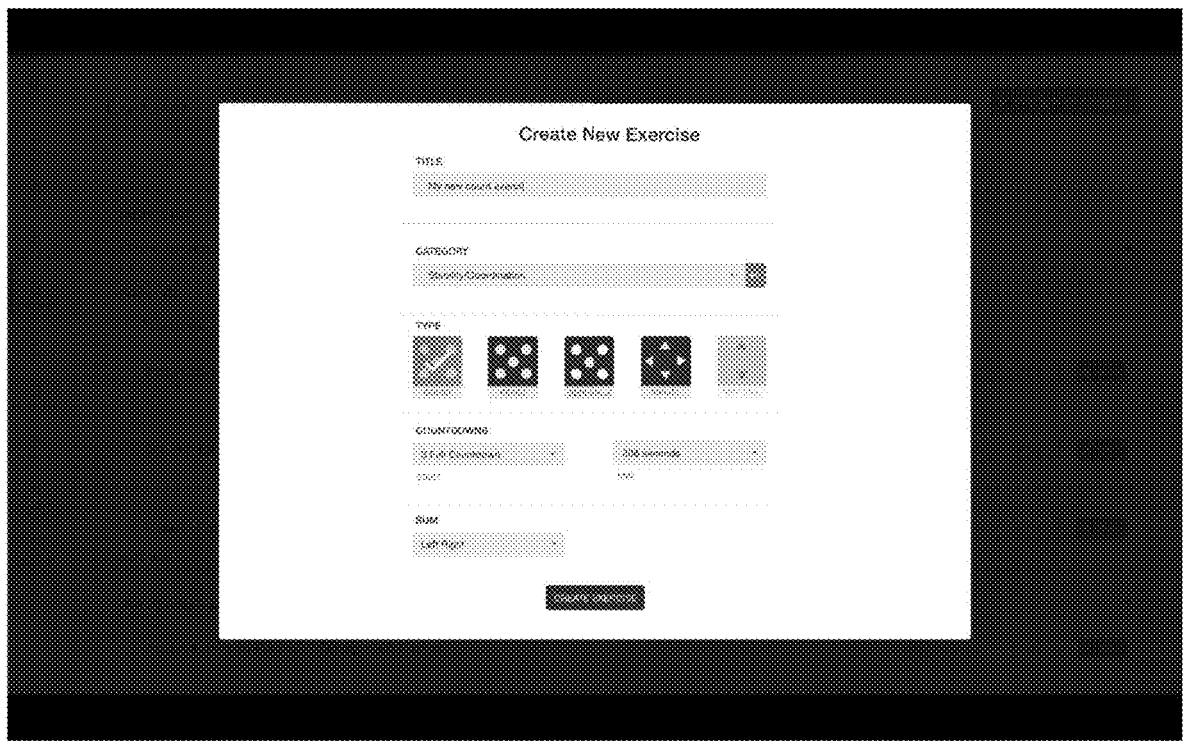
FIG. 13 shows an embodiment of a create exercise screen for a count drill for use in the system.

FIG. 13 shows use of the create exercise screen to create a count drill. Count drills are the most straightforward type of exercise in the system 1000. The count drill counts the sum of the completed steps within a particular time period. The system 1000 can sum left touches, right touches, and total sum of both left and right touches. The system 1000 determines whether a touch should count. During or after the exercise, the system 1000 displays the count drill data.

Figure 14:
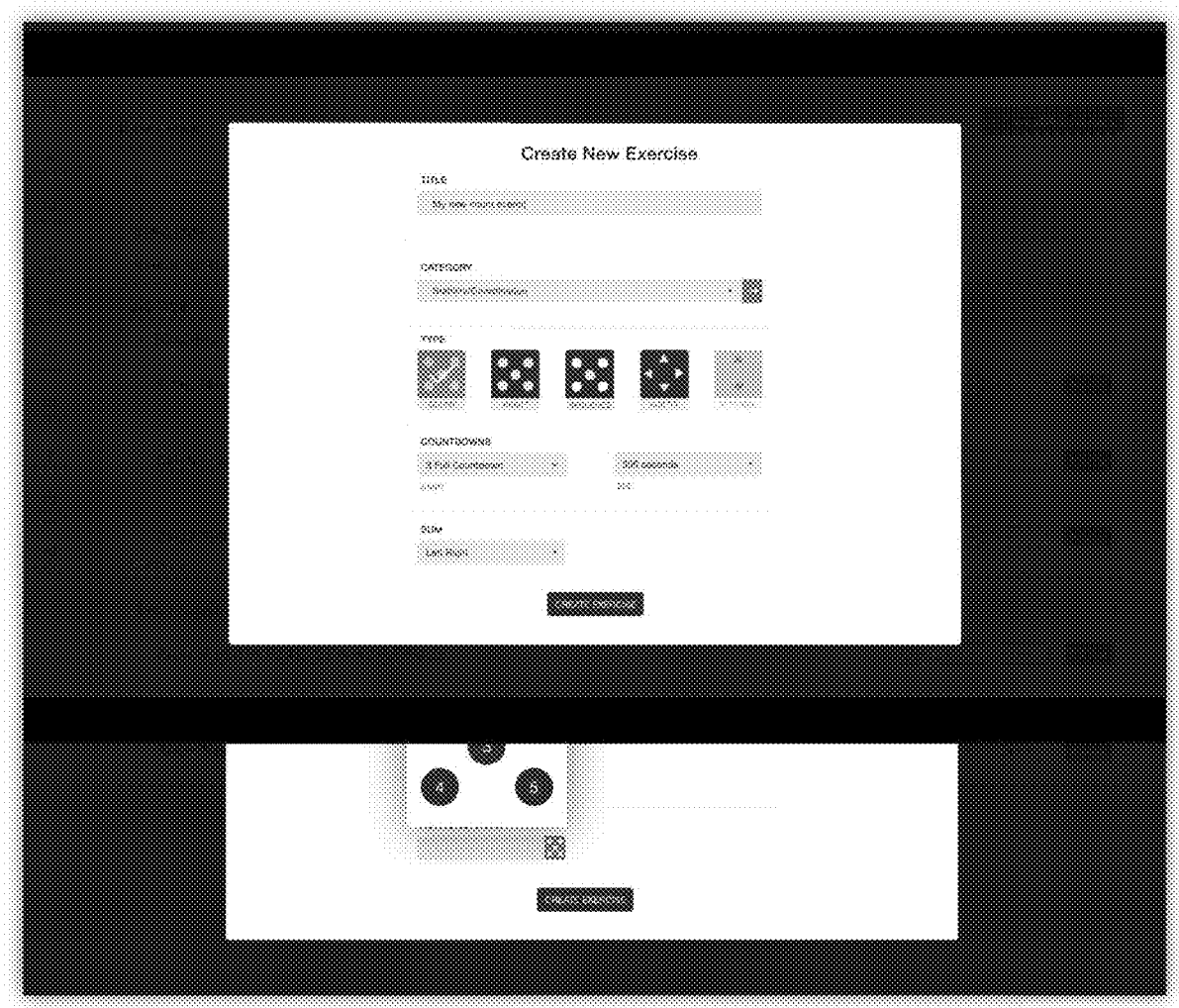
FIG. 14 shows an embodiment of a create exercise screen for a react drill for use in the system.

FIG. 14 shows use of the create exercise screen to create a react drill. In the react drill, the athlete/patient reacts to colors: the admin/location administrator should select to which colors an athlete/patient should react. Features of the react drill include:
 delay: the delay between displaying actions.
 prompt type: solid or flash. when prompt type is solid that the sensor location is highlighted until the athlete/patient presses on it. When prompt type is flash the admin/location adminstrator must enter how long the sensor location should be highlighted.
 isolated sensors: on/off. if isolated sensors is on than the admin/location administrator should select which sensors will be used. If it's off, then all sensor will be used.
 Neurocognitive React. There are 3 values from which the admin/location administrator can select:
 Off. When off is selected, there are no extra details that the admin/location adminstrator should fill out.
 array. The admin/location administrator must select 1 react to color and multiple don't react to colors. When this type of exercise is performed all sensor location are highlighted and the athlete/patient must press the correct color. If the athlete/patient doesn't press the correct color, it is counted as an error.
 go/no-go. The admin/location administrator can select one or more react to colors and one or more don't react to colors. These colors will be shown interchangeably and the athlete/patient should react only when one of the react to colors are shown. When this type of neurocognitive exercise is selected, the prompt type can be only flash and the admin/location administrator should enter the period of time that a sensor location should be highlighted.

Figure 15:
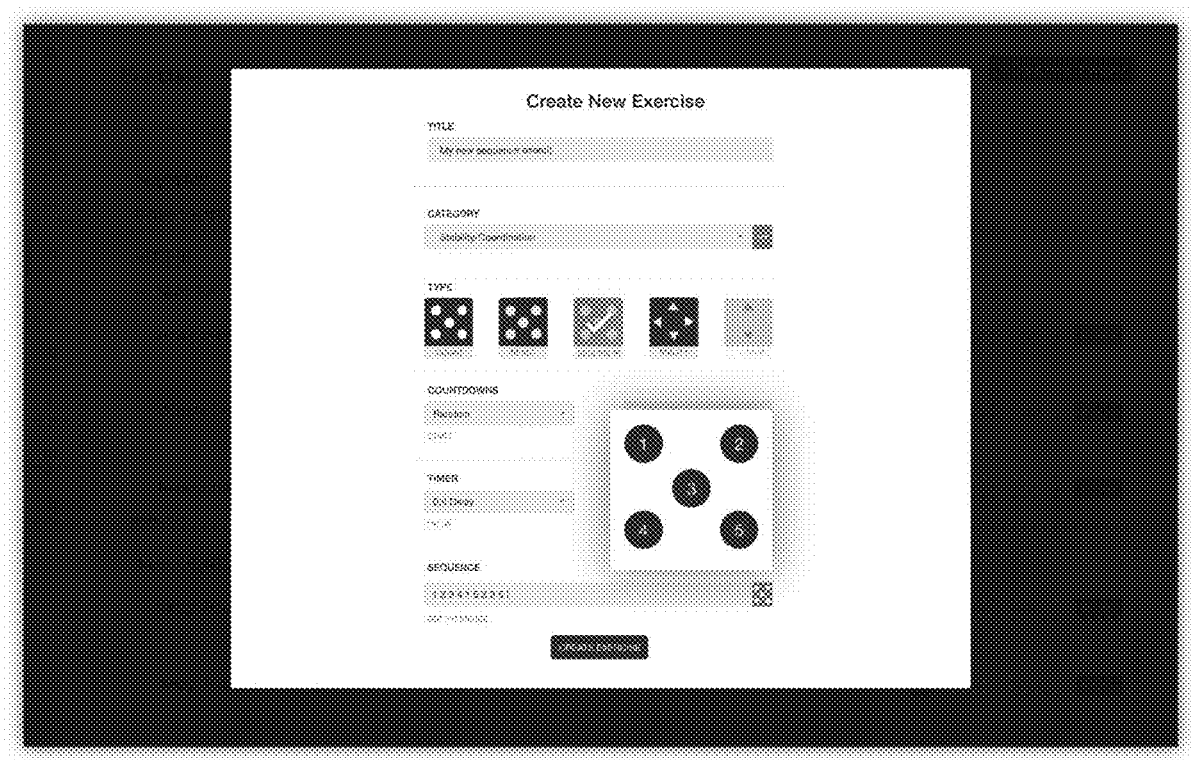
FIG. 15 shows an embodiment of a create exercise screen for a sequence exercise for use in the system.

FIG. 15 shows use of the create exercise screen to create a sequence exercise. The sequence exercise is similar to the count exercise, but the dots are pressed in a certain sequence. The sequence is typically done separately for each leg (left or right), but sequence exercises can be executed as single leg hops which entails using the right or left leg. Features of the sequence function include: delay: the delay between displaying actions; and the sequence in which the sensor are highlighted.

Figure 16:
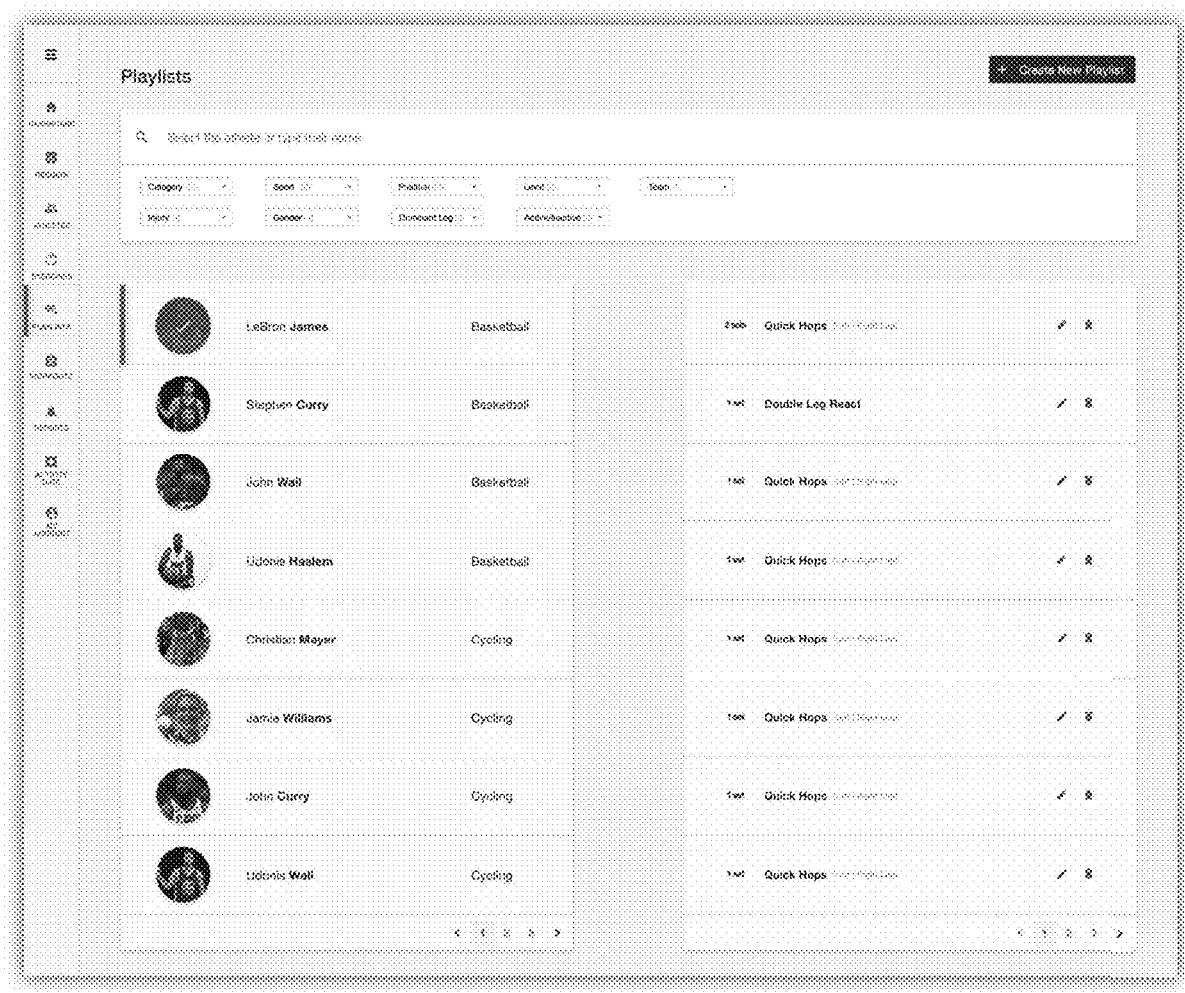
FIG. 16 shows an embodiment of a screen for a playlist function for use in the system.

FIG. 16 shows an exemplary screen of a playlist function. The playlists function allows the admin/location administrator to better customize the exercises for each athlete/patient. Playlist function can include the option to create playlists for each profile and create custom settings for each exercise without affecting the original settings or other playlists that already contain that exercise.

An admin/location administrator can use the playlist screen to create new playlists. When creating a new playlist, options include:
 selecting the exercises that the admin/location adminstrator wants to add to the playlist.
 selecting the order in which the exercises are performed.
 specifying the number of times an exercise must be performed (number of sets).
 specifying if the playlist is automated. An automated playlist automatically starts the next exercise.
If a playlist is automated, it can: specify if the playlist is a circuit (perform 1 exercise then move to the next exercise in the playlist) or if it should be performed in straight sets, i.e. all programmed sets of the exercise are completed before moving to the next exercise; specify the rest time between exercises (duration between when the last exercise has finished and the next one starts); assign it to athletes; edit exercise settings.

Editing an existing playlist may include the following programming options:
- change the order of the exercises
- add/remove exercises from playlist
- change the rest time
- change if a playlist is a circuit
- change if a playlist is automated
- assign it to athletes
- edit exercise settings.

Figure 17:
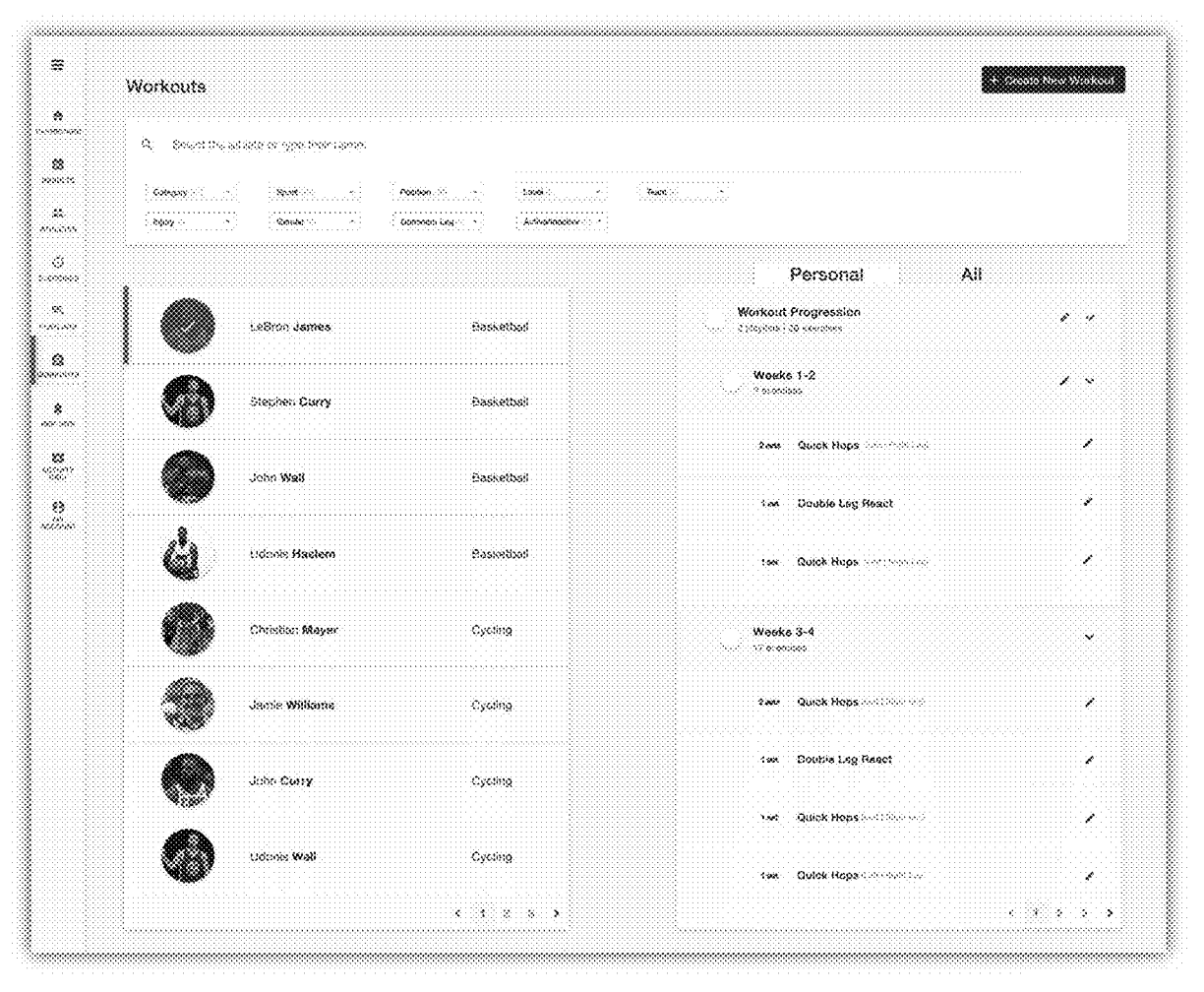

FIG. 17 shows an exemplary screen for a workout function. This feature allows the admin/location administrator to create custom protocols that an athlete/patient can perform based on their improvement or progress. On the workouts screen, an admin/location administrator is be able to:
- create a new workout. A workout/protocol has:
  - a name.
  - a list of playlists.
- When creating a new playlist, an admin/location administrator:
  - enters the playlist name.
  - selects the exercises that it wants to add to the playlist.
  - can edit the settings for the exercises without affecting the original settings or other playlists that already contain that exercise.
  - can select the order in which the exercises are performed.
  - can specify the number of times an exercise must be performed (number of sets).
  - can specify if the playlist is automated. An automated playlist automatically starts the next exercise.
  - can specify how many times the playlist is performed over a period of days, weeks, or months.
  - can select whether a playlist is automated by specifying if the playlist is a circuit (perform 1 set than move to the next exercise) or straight sets (perform all sets of the exercise before moving to the next exercise in the playlist).
  - if a playlist is automated then it can specify the rest time between exercises. Duration between when the last exercise has finished and the next one starts.
  - assign it to athletes/patients.
- When editing an existing playlist, an admin/location administrator can:
  - change the order of the exercises.
  - add/remove exercises from a playlist.
  - edit the settings for the exercises without affecting the original settings or other playlists that already contain that exercise.
  - change the rest time.
  - change if a playlist is a circuit.
  - change if a playlist is automated.
  - assign it to athletes.
  - add the workout to athlete/patient profiles.
  - delete existing workouts.

Figure 18:
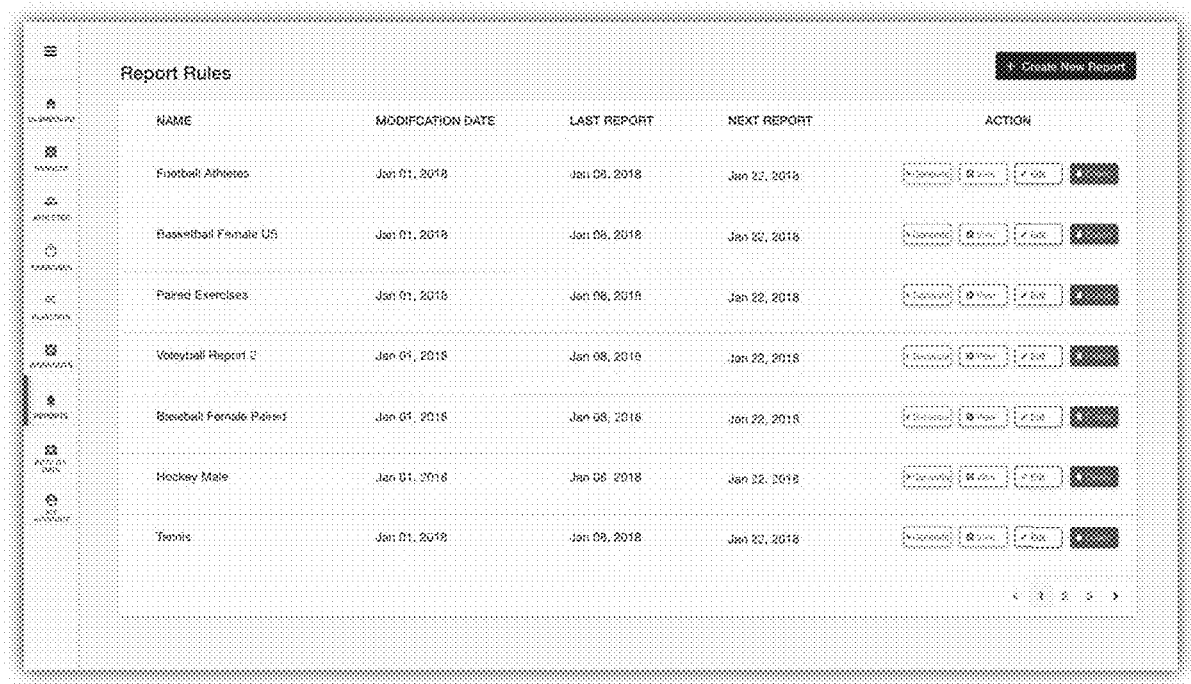
FIG. 18 shows an embodiment of a screen for a reports function for use in the system.

FIG. 18 shows an exemplary screen for a reports function. On the reports screen an admin/location administrator can:
- view all report rules: when it was modified, when was the last report generated, and when will the next report be generated.
- execute existing report rule—this action will generate a report that will be sent to the admin/location administrator's email.
- edit an existing report rule.
- view all reports generated for a specific rule. If a report is selected, it will open the document that was sent to the admin/location administrator's email.
- delete an existing rule.

The system 1000 can include an iPad screen. On the iPad screen, an admin/location administrator can:
- select which athlete/patient profile should sync with a location's iPads. By default, all profiles are selected.
- select which exercises should sync with a location's iPads. By default, all active exercises sync with the iPad. If an exercise is inactive, but it's in a playlist, then that exercise syncs to the iPad.
- view when the iPad has last synced with the cloud.
- restrict access to data to iPads. If an admin/location administrator doesn't want an iPad to sync with the cloud, then the admin/location administrator can restrict an iPad's access.

The system can include an Activity Data screen. On the activity data screen, an admin/location administrator can:
- add to athlete/patient profile exercises/activities that were not performed on the Quick Board platform, e.g. Bench press, sprints, sleep, etc.
- edit activity data.
- Distinguish certain exercises as Tests so that the system 1000 distinguishes testing, training and rehab results.
- Classify a custom exercise as a testing, training or rehab exercise.

The system 1000 can include a My Account screen. On My Account screen, an admin/location administrator can:
- edit personal details.
- set predefined values, e.g. athlete/patient category, team, sport, position, etc.
- view number of active/inactive athletes for a location.
- view billing details:

The system 1000 can include a billing screen. The billing screen is accessible only to admin/location administrators. On the Billing screen, an admin/location administrator can:
- view past invoices.
- view an estimated value for next invoice.
- change billing/card details.
- view remaining days until next invoice.

The system can include a Reports function. Options include:
- Autogenerate Report Option: automatically emails a report when an athlete/patient completes an assigned workout/protocol. This will ensure the reporting works in real-time and delivers immediately after workouts/protocols. This will save therapists time from accessing the web app to export it to upload patient info to a medical record. Also, it will engage athletes and active individuals who want to see how they did immediately after.

Mobile Application

The system 1000 can include a mobile application function. On the mobile app function, athletes/patients can access their results, progress, ratings, overall ranking, their ranking for each exercise, completed workouts/protocols, and so forth. The system 1000 can send engaging content such as next workout/protocol reminder, new exercise records by the athlete/patient or another athlete, rankings updates and so forth. The user can also receive a weekly progress report, either by user selection or by auto-generation by the system 1000.

Figure 19:
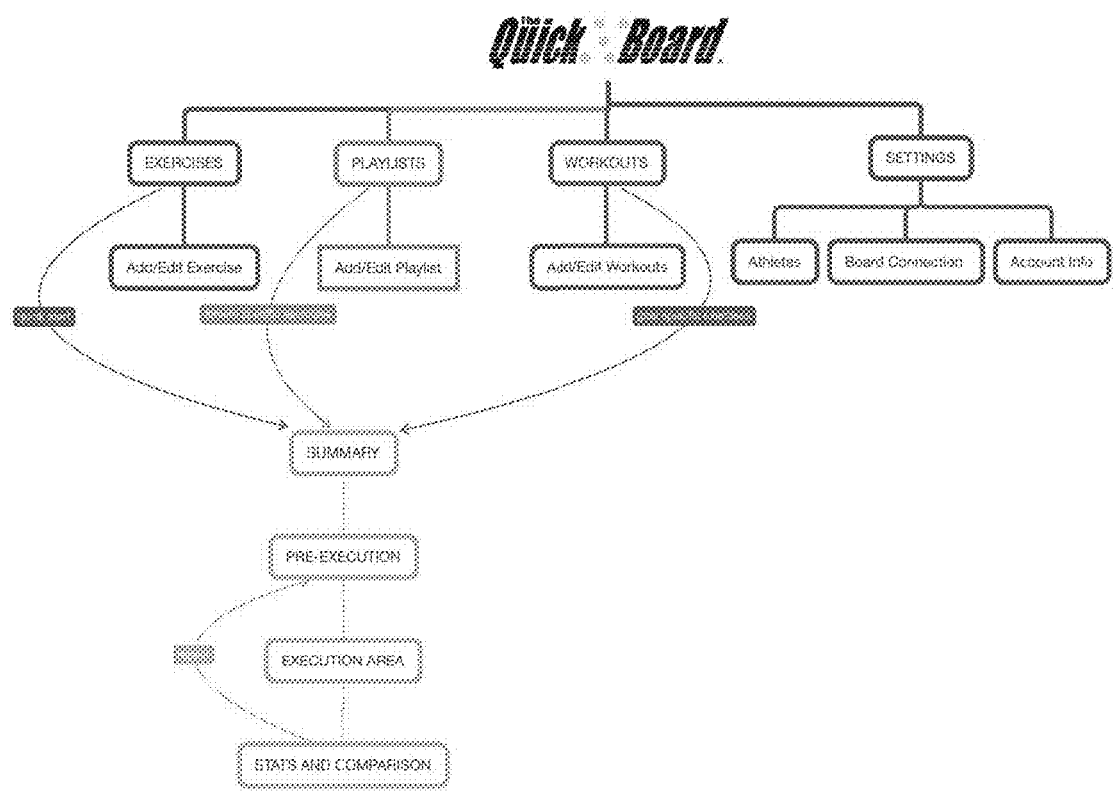
FIG. 19 is a schematic diagram of an embodiment of flow for a mobile app for use in the system.

FIG. 19 shows a schematic diagram of an exemplary flow for a mobile app function. The various functions of the mobile app are described below with reference to exemplary mobile app screens.

Figure 20:
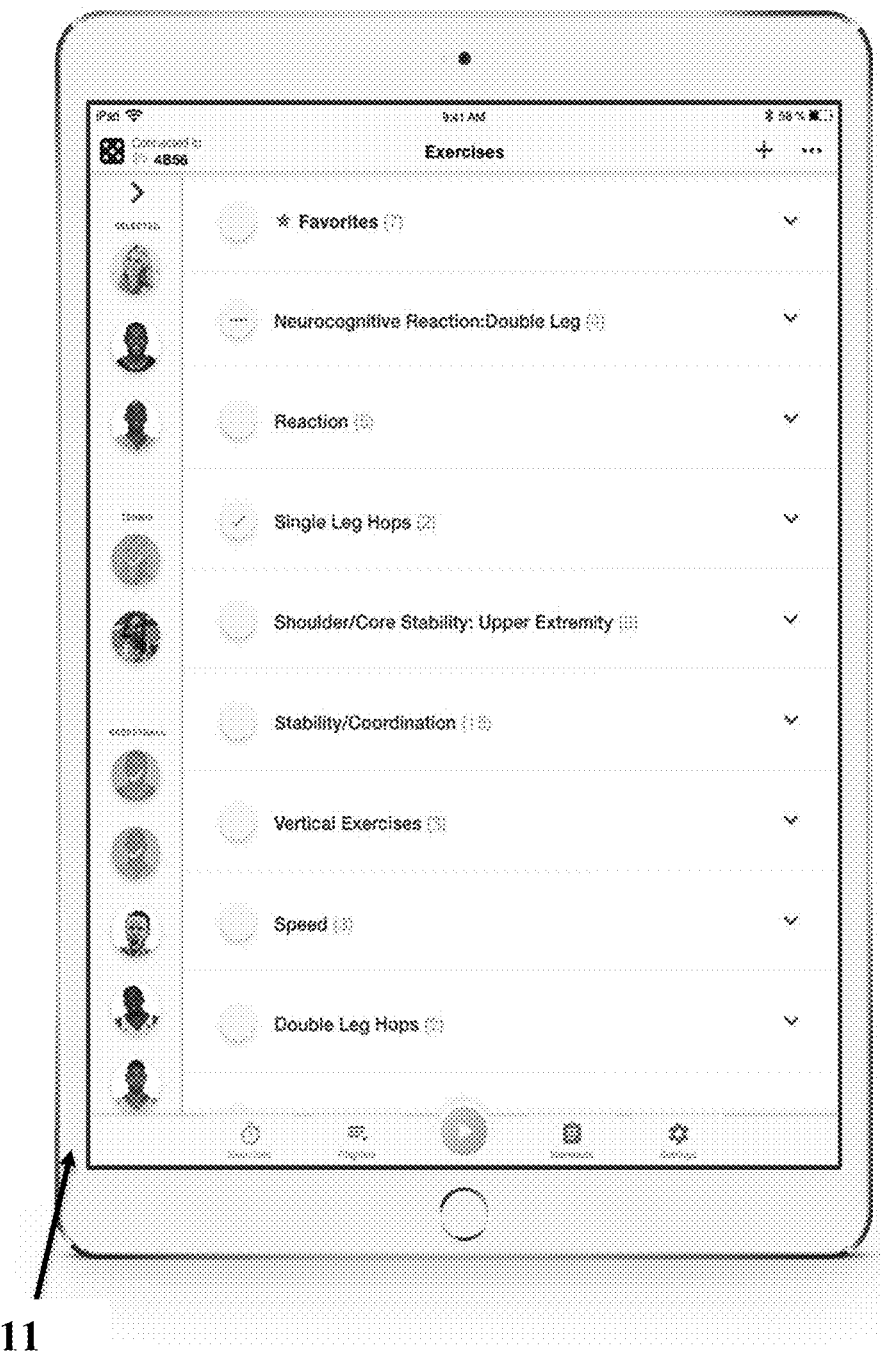
FIG. 20 shows an embodiment of a screen for a mobile app exercise function for use in the system.

FIG. 20 shows an exemplary screen for a mobile app exercises screen function. The mobile exercise screen shows all the exercises available to the location administrator. Exercises are specific for each location administrator's device. Which exercises are available to each location administrator's device can be configured on the web platform. Exercises are grouped by exercise category. Exercises can be selected in a specific order, representing the order they will be executed in by the athlete/patient. All the exercises in a particular category can be selected by selecting the category. Exercises can be selected as a favorite so they show up at the top of the list, in a separate category. Each exercise can have a video, either provided by default or recorded by an admin/location administrator. An admin/location administrator can delete the video, record a video or use a video from the device's library. Videos can be downloaded to the device for offline use. Exercises are represented on screen by the exercise name, exercise type and key exercise settings specific to the exercise type. Selected exercises are marked by a number next to their name, representing their place in the order of execution.

Athletes/patients available on the device may be shown on a side panel on the left of the screen. Specific exercises show up for each device. The athletes/patients that are going to perform the exercises can be selected on the mobile exercise screen.

The athletes/patients are grouped into categories. When the athlete/patient panel is collapsed, athletes/patients are represented by a photo. If the athlete/patient does not have a photo, their initials are shown. The panel can be expanded so that the athlete's/patient's full name appears on screen.

Figure 21:
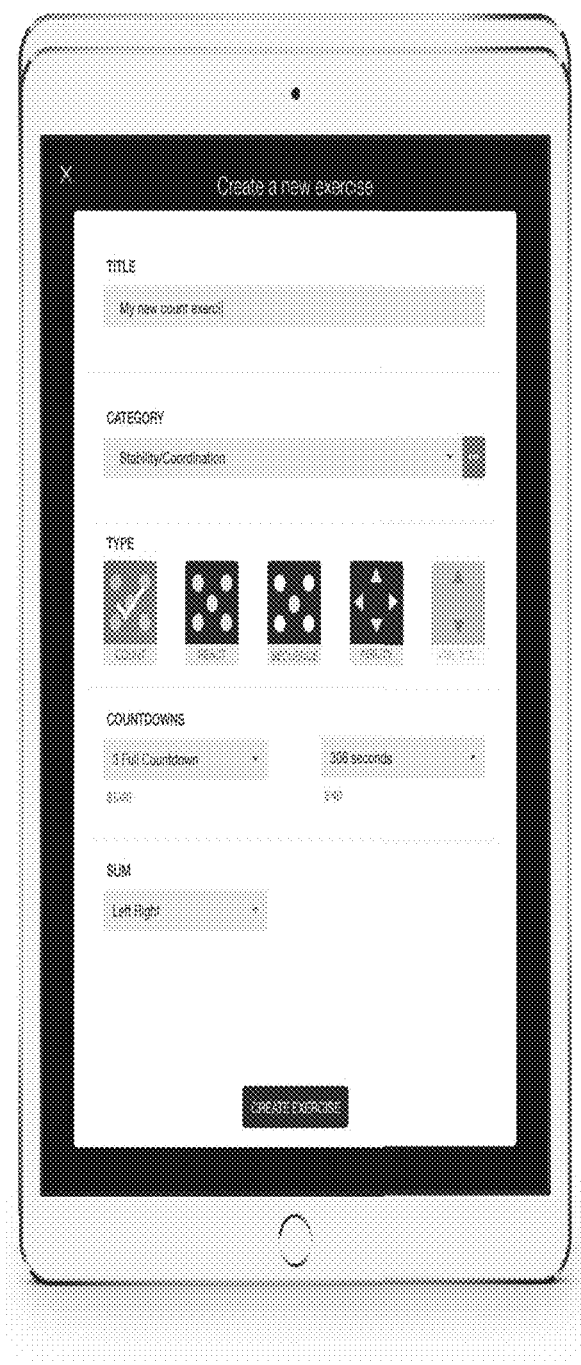
FIG. 21 shows an embodiment of a mobile app screen for creating a new exercise for use in the system.

FIG. 21 shows an exemplary mobile app screen for creating a new exercise. In FIG. 21, the screen is being used to create a count exercise. Exercises can be created and edited on the Add Exercise Screen. The details that can be edited on this page are:

The exercise's name: Used to identify the exercise.

The exercise's category: Used to group similar exercises together.

The exercise's type: Possible Exercise types include: count, react, sequence, agility and vertical. Each of them has a specific execution flow.

The exercise's start type: Describes how the exercise start. Either after a fixed countdown between 1-5 seconds, random start or start automatically when the user starts using the board.

The exercise's end type: Describes when an exercise is done. Either after a programmed number of touches or after a programmed timeframe.

There are 5 types of exercises: count, react, sequence, agility, and vertical. Each of them will be described below, as follows, with reference to the mobile app.

1. COUNT:

This type of exercise asks the athlete/patient to press certain sensors as fast as possible in a specific way.

The settings for count exercises are:

Countdown: start/end

Sum type: Sum All or Left/Right

Describes how the athlete's/patient's result is saved, either a sum of both his legs or each leg's result saved separately.

2. REACT:

This type of exercise asks the athlete/patient to look at what is displayed on the device and react accordingly, touching the appropriate sensors on the board. The settings for react exercises are:

Countdowns: start/end

Neurocognitive: Go/No-Go, Array, or OFF

With the setting on Go/No Go, only one sensor light on the screen will light up at a time. The sensor light may be either a correct or incorrect color. The athlete/patient is asked to recognize if the color is correct and touch the corresponding sensor on the board. If the sensor light is an incorrect color, the athlete/patient should ignore it and not touch any sensors on the board.

When selecting Array, all the active sensor lights on the screen light up at once with different colors. Only one color is correct. The athlete/patient is asked to recognize the correct color and touch the sensor on the board corresponding to that color. When neurocognitive react is turned off, only one sensor lights up on the screen at once and the athlete/patient reacts to the corresponding sensor on the board.

React/Don't react (to colors): select/deselect colors

Only applicable when neurocognitive react is on.

React colors represent the correct colors the athlete/patient should react to by touching the board.

Don't react to colors represent the colors the athlete/patient should ignore (and don't touch any sensors) during the exercise.

Delay (0.1→5.0 seconds): Represents the time in seconds between two consecutive sensors lighting up on screen. It is measured from the time a sensor light turns off until the next sensor light turns on. When delay is turned off, there is no delay time before the next sensor light turns on.

Prompt type: Solid or Flash. When the prompt type is set to Flash, the admin/location administrator can select how many seconds a sensor light stays lit up. Flash type is measured from the time a sensor light turns on until it turns off. Flash time can also be set to dynamic. When flash time is set to dynamic, the exercise starts with a default flash time and decreases if the athlete/patient is doing well and increases if they are doing poorly. When the prompt type is set on Solid, the athlete/patient doesn't have any time restriction for touching a sensor. The sensor light stays lit up until it is touched.

Isolated react: ON/OFF. Isolated react gives the admin/location administrator the option of limiting which sensor lights turn on. When it's turned off, all sensor areas are active.

Active sensors: numbers from 1→5 representing each of the sensors. Only applicable when isolated react is turned on. Represents which sensor lights that could light up.

3. SEQUENCE:

This type of exercise asks the athlete/patient to touch the sensors in a specific, predetermined order and tracks user performance accuracy. The settings for sequence exercises are:

Countdowns: start & end

Delay (0.1→5.0): Represents the time in seconds between two consecutive sensors lighting up on screen. It is measured from the time a sensor light turns off until the next sensor light turns on. When delay is turned off, there is no delay time before the next sensor light turns on.

Prompt type: Solid or Flash. When the prompt type is set to Flash, the admin/location administrator can select how many seconds a sensor light stays lit up. Flash type is measured from the time a sensor light turns on until it turns off. When the prompt type is set on Solid, the athlete/patient doesn't have any time restriction for touching a sensor. The sensor light stays lit up until it is touched.

Sequence. Represents what sensors the athlete/patient has to touch and in what order.

4. AGILITY:

This type of exercise displays arrows or a wildcard symbol on screen. The athlete/patient has to react accordingly to which direction the arrow is pointing or if the wildcard symbol displays on-screen he has to a predetermined action such as jump or do a push-up.

Delay. Represents the time in seconds between two consecutive arrows showing up on the screen. It's measured from the time an arrow disappears from the screen until the next arrow is shown. When delay is turned off, there is no time with no arrows on screen.

Arrow sequence or react options. Represents the possible arrows that can show up on screen. The order of the arrows can be predetermined (and known by the athlete) or random (and the athlete needs to react on the spot to what is happening on screen).

Neurocognitive: Go/No-Go, Array, or OFF

With the setting on Go/No Go, only one arrow appears on the screen at a time. The arrow can have either a correct or incorrect color. The athlete/patient is asked to recognize if the color is correct and respond accordingly. If the arrow has an incorrect color, the athlete/patient should ignore it.

When selecting Array, all the active arrows on the screen light up at once with different colors. Only one color is correct. The athlete/patient is asked to recognize the correct color and respond accordingly.

When neurocognitive react is turned off, only one arrow appears on the screen at once and the athlete/patient responds accordingly.

React/Don't react (to colors): select/deselect colors

Only applicable when neurocognitive react is on.

React colors represent the correct colors the athlete/patient should react to.

Don't react to colors represent the colors the athlete/patient should ignore during the exercise.

5. VERTICAL:

This type of exercise measures the athlete/patient's air time and estimates jump height. The athlete/patient can start on the sensors (with one or both feet) or off the board. The athlete/patient jumps as high as possible and must land on one or more sensors.

Figure 22:
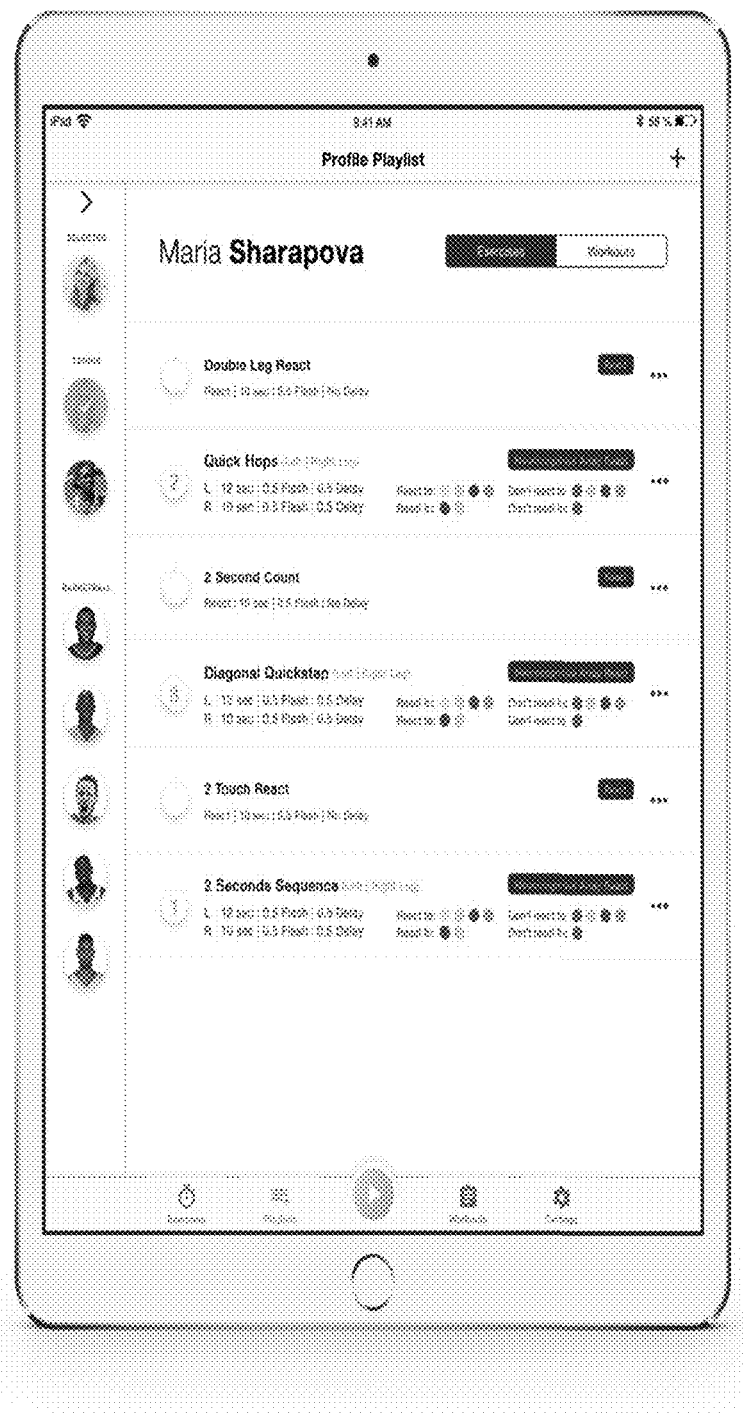
FIG. 22 shows an embodiment of a mobile app screen for a profile playlist for use in the system.

FIG. 22 shows an exemplary screen for a profile playlist in a mobile app version of the system 1000. The profile playlist screen is designed to show the specific exercises that were designed and designated specifically for the athlete/patient by an admin/location administrator or Quick Board's artificial intelligence.

On the screen the admin/location administrator selects the athlete/patient on the left side of the screen from the list of athletes/patients, then the exercise and workout recommendations are displayed for the selected athlete/patient which have been recommended by Quick Board's artificial intelligence and machine learning software. An admin/location administrator may also manually select exercises and workouts for that athlete/patient.

On the top of the screen, the admin/location administrator can press the "add exercise" button. That brings up the entire list of exercises and workouts/protocols available on the device. The admin/location administrator can choose which exercises they would like to add to the athlete/patient's profile.

An admin/location administrator has the ability to automate an entire playlist:

Select the exercises and the order they should be performed.

Select the rest time between exercises.

Activate circuit playlist and select the number of circuit sets.

A. Turning circuit playlist on will cause all the selected exercises to run once in the order they were selected. The entire process is repeated as many times as the circuit sets number indicate.

B. If circuit playlist is turned off, then the admin/location administrator can select the number of sets for each exercise. Exercises are executed in the order selected by the admin/location administrator. The exercise changes when the number of individual predetermined sets are completed for the current exercise.

If the playlist is not automated, the athlete/patient has the ability to perform as many sets as they want and execute the exercises in any order.

Figure 23:
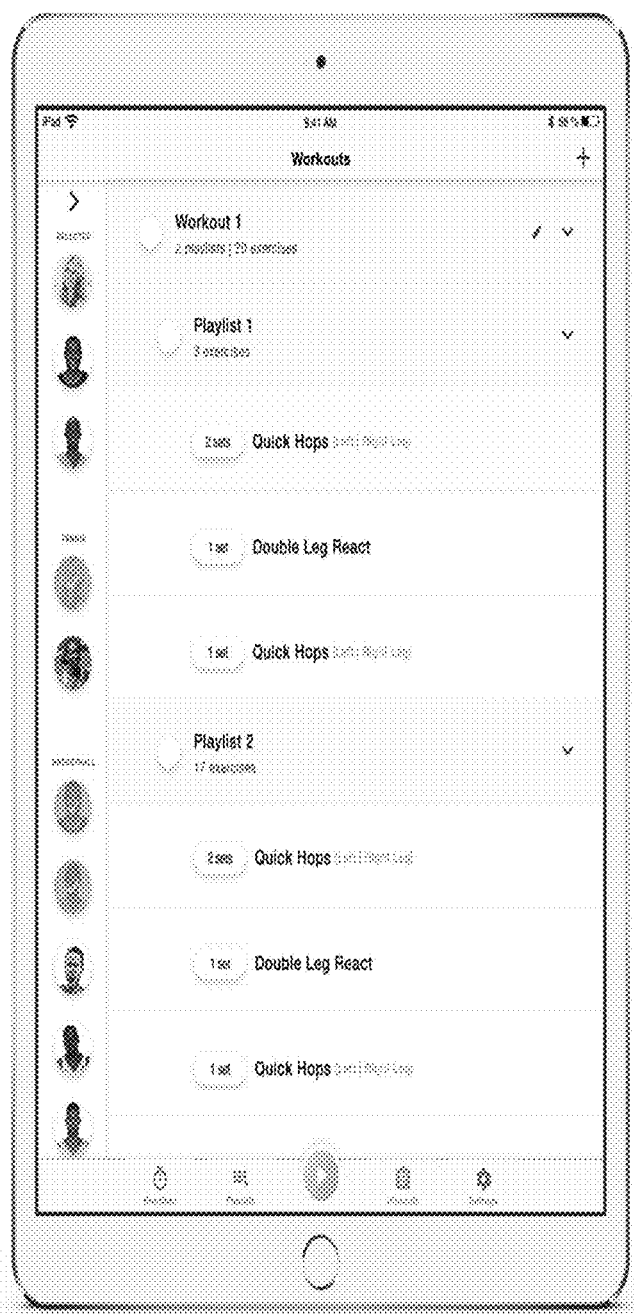
FIG. 23 shows an embodiment of a mobile app screen for a workouts page for use in the system.

FIG. 23 shows an exemplary screen for a workouts page in a mobile app version of the system 1000. The purpose of the workouts screen is to show all the workouts available. An admin/location administrator can select multiple athletes/patients from the left menu and the workout they want the athletes/patients to perform.

Workouts are designed around different goals (getting quicker, improving coordination), activities (warm-up, cool-down) or rehabilitation protocols for specific injuries.

A workout contains multiple playlists. Playlists can help structure a workout in multiple ways:

A workout can be split up into a week by week progression. Each playlist representing a week.

The same workout can have multiple difficulty levels. Each playlist represents a level (beginner, advanced, pro).

A workout can have different exercises based on the day of the week. Each playlist representing a different day.

An admin/location administrator can assign workouts to specific athletes/patients based on their needs.

The admin/location administrator can either make all the playlists of the workout available at once or choose a specific way to unlock each playlist:

Unlock the next playlist based on a result goal. When an athlete/patient achieves the result goal for the next level, it's unlocked automatically.

Unlock the next playlist based on number of attempts. When an athlete/patient has attempted the current playlist enough times, the next one is automatically available.

Unlock the next playlist based on a specific time frame. A new playlist is made available every day, every week, or every month.

Each playlist contains exercises with specific settings for that particular workout/playlist. Every exercise is assigned a number of sets, representing how many times an exercise needs to be performed.

Multiple Athletes can perform the same workout at once.

A workout session can be automated. That means exercises start automatically without the user needing to do anything:

The admin/location administrator sets a rest time between exercises. After an exercise ends the rest time countdown appears on the screen, letting the athlete/patient know when the next exercise is about to start.

Before each exercise, the software lets the athlete/patient know who is next to perform an exercise, the exercise they will perform, and a demo video of the next exercise is played on the rest time screen.

The device goes through all the exercises in the workout and through all the selected athletes one by one.

If the next athlete/patient is ready to start the exercise and doesn't want to wait for the rest time countdown to expire, they can press the "start now" button. That brings the countdown down to 3 seconds so the athlete/patient can prepare to start.

If the next athlete/patient is not ready to start the exercise, he can pause the countdown.

If the next athlete/patient doesn't want to do the specific exercise or they are not present, the exercise can be skipped.

A new workout can be created on the device by pressing the + button. Doing this will bring up the create workout screen.

To create a new workout the user needs to add the following:

A name for the workout.
Add one or more playlists to the workout.
Name each individual playlist.
Add one or more exercises to the playlist.
Assign the number of sets for all the exercises.

Once a workout is created, the workout syncs across all of the account devices and to the web platform. The workout can be edited and assigned to athlete/patient profiles.

Figure 24:
FIG. 24 shows an embodiment of a mobile app screen for settings for use in the system.

FIG. 24 shows an exemplary screen for a settings screen in a mobile app version of the system 1000. The settings screen allows the user to configure various parts of the app.

The admin/location administrator can assign a specific name to the current device. That way it can be easily recognized on the web platform. Making assigning specific exercises and specific athletes/patients to a device faster.

Response Mode:

The device can either use the touch screen for user input, the camera for the Augmented Board, or connect to a sensor board via Bluetooth Low Energy:

Touch Screen: With touch screen input enabled, exercises can test the athlete's/patient's coordination and speed when using his upper limbs. A representation of the board is displayed on the screen and the athlete/patient presses the sensor areas.

AR Board: (Lite Version) The device's camera is used to track shoes and detect the presence of shoes on the sensor areas. (Extended Version) If a pair of wearable devices are assigned to an athlete/patient profile and they are turned on, then the software will sync with the wearables for confirming "sensor presses" and collecting additional metrics during exercises.

Sensor Board with Bluetooth: With a board connected, the touch screen elements are disabled. The only input is from the Bluetooth Low Energy sensor board. After selecting Sensor board with Bluetooth option, the admin/location administrator sees a list of available sensor boards they can connect to.

Board Type:

The admin/location administrator can select whether they want data collected from 5 or 7 sensor locations. Board type is an active setting for all response modes including AR Board Extended Version.

Exercise Settings:

Progress Bar Settings: the admin/location administrator can activate or deactivate the progress bar capability by exercise type, i.e. Count, Sequence, React, and Neurocognitive React and set the desired data comparison.

The admin/location administrator can access the entire list of athletes/patients available on the device. Selecting "Athletes" will take the user to the Athletes screen where they can add, edit, or delete athlete profiles.

Force Resync Result→if anything has been changed from the Admin Web App, and the updated information has not been pushed to the device, a forced resync can be performed.

Log Out→Logs out the active user and redirects the user to the login screen.

Figure 25:
FIG. 25 shows an embodiment of a mobile app screen of an athlete screen for use in the system.

FIG. 25 shows an exemplary screen for an athlete screen in a mobile app version of the system 1000. All available athletes (specific for each device) are shown on the screen. The athletes are grouped into athlete categories. Inside the athlete categories, athletes are sorted by last name and represented by: full name, sport, position, dominant leg and team. Athletes can be filtered using the search field. From this screen an admin/location administrator can create more athletes.

Figure 26:
FIG. 26 shows an embodiment of a mobile app screen for creating a new athlete profile for use in the system.

FIG. 26 shows an exemplary screen for creating a new athlete profile in a mobile app version of the system 1000. An admin/location administrator can create an athlete on the device using this screen. The fields can include:

First and last name: identify the athlete.
Athlete photo: shown everywhere an athlete is displayed. It's not mandatory to add a photo. If no photo is used, the athlete's initials are used instead.
Category: group similar athletes together.
Personal Info: Date of birth, height, weight, gender, email (entered to receive ratings and progress reports)
Sport: select from a list of sports. Athletes can be filtered by specific sports, making finding an athlete easier.
Position: the position the athlete plays in the selected sport. This field is inactive if the selected sport does not have positions.
Team: the team the athlete plays for.
Level: selections are provided to identify an athlete's experience, e.g. High School, College, Pro, Recreational. The clinics app provides a different list of levels, e.g. Sedentary, Recreational Non-Competitive, Recreational Competitive, to provide accurate patient population analysis.
Dominant leg: Provides insight for bilateral deficits that can be attributed to dominance.
Injury: Add injuries to an athlete/patient profile to properly segment training and rehabilitation data. Provides valuable injury data aggregation capabilities.

Figure 27:
FIG. 27 shows an embodiment of a mobile app screen of a playlist overview for use in the system.

FIG. 27 shows an exemplary screen for a playlist overview in a mobile app version of the system 1000. Pressing the start button from the exercises/playlists/workouts screen brings up the "Exercises Overview"/"Playlist Overview"/"Workout Overview" screen. The purpose of the playlist function is to give the athlete/patient a quick overview of the exercises, playlist, or workout. The athlete/patient can see the selected exercises and the order they are in. All of the selected athletes/patients are listed on the screen as well. This is the last chance to reorder, add and remove exercises. Specific settings for automated playlists and automated workouts can also be modified. At the bottom of the screen the athletes/patients can see a time estimate of how long it will take to complete all of the exercises.

Figure 28:
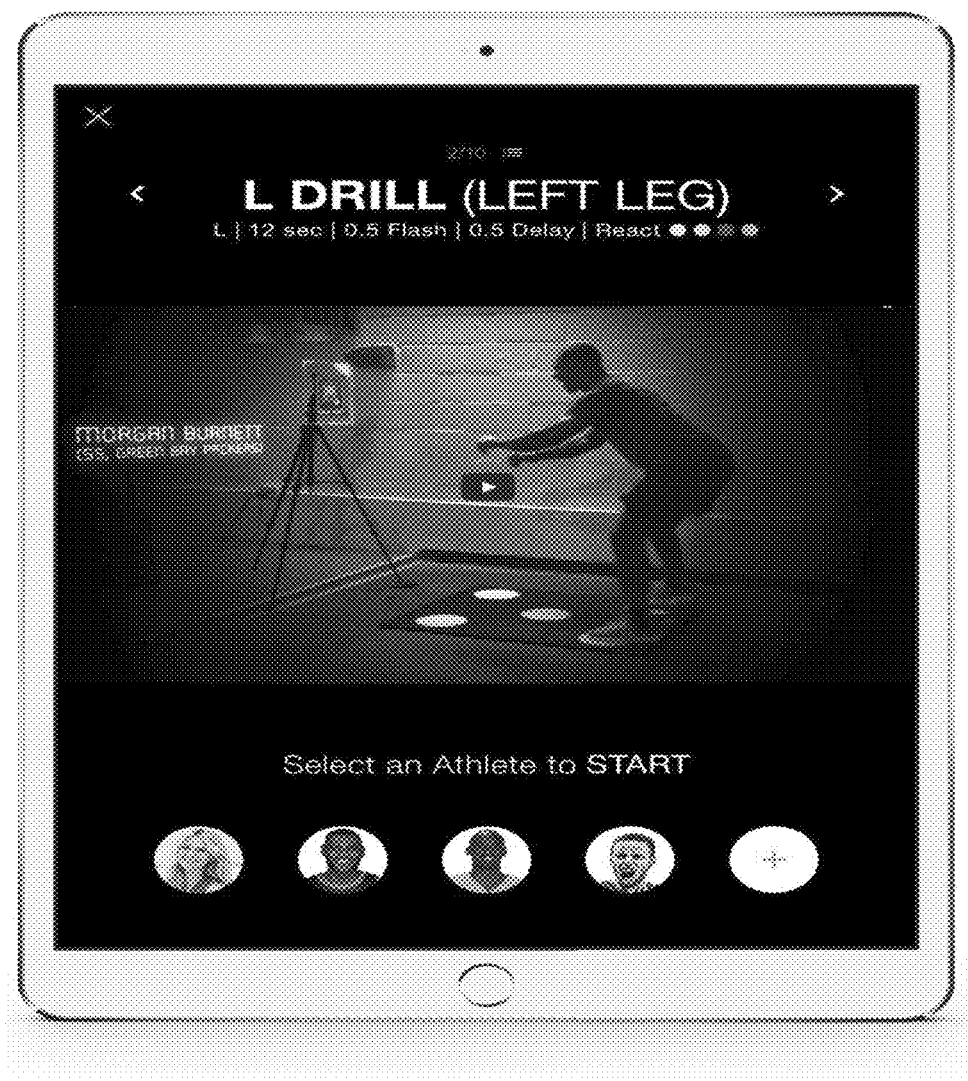
FIG. 28 shows an embodiment of a mobile app screen of an athlete/patient selection function for use in the system.

FIG. 28 shows an exemplary screen for an athlete/patient selection function in a mobile app version of the system 1000. From this screen, the athlete/patient will see a complete overview of the exercises they are about to start. In the upper part, the user can select the playlist icon to check the list of all exercises that will follow. By pressing one of the two arrows, < or >, the athlete/patient can move through all of the exercises from the current workout and quickly change the selected exercise. In the middle of the screen, a demo video of the upcoming exercise will play. If a demo video hasn't been uploaded or downloaded, a short descriptive text of the exercise will appear in the same place. In the footer, the next athlete/patient will be pre-selected for the upcoming exercise, ticked and on an orange background. The athlete/patient can be changed by tapping on a different profile or by adding a new one with the + icon. If a playlist or workout has been selected, the number of sets for each exercise will be shown and the remaining athletes are shown in the order they will have to execute the exercise.

When the rest time is about to expire during an automated playlist or workouts, the start countdown is displayed larger so it can be seen from across the room. Also, loud beeps play, letting the athlete/patient know that the next exercise is about to start.

Figure 29:
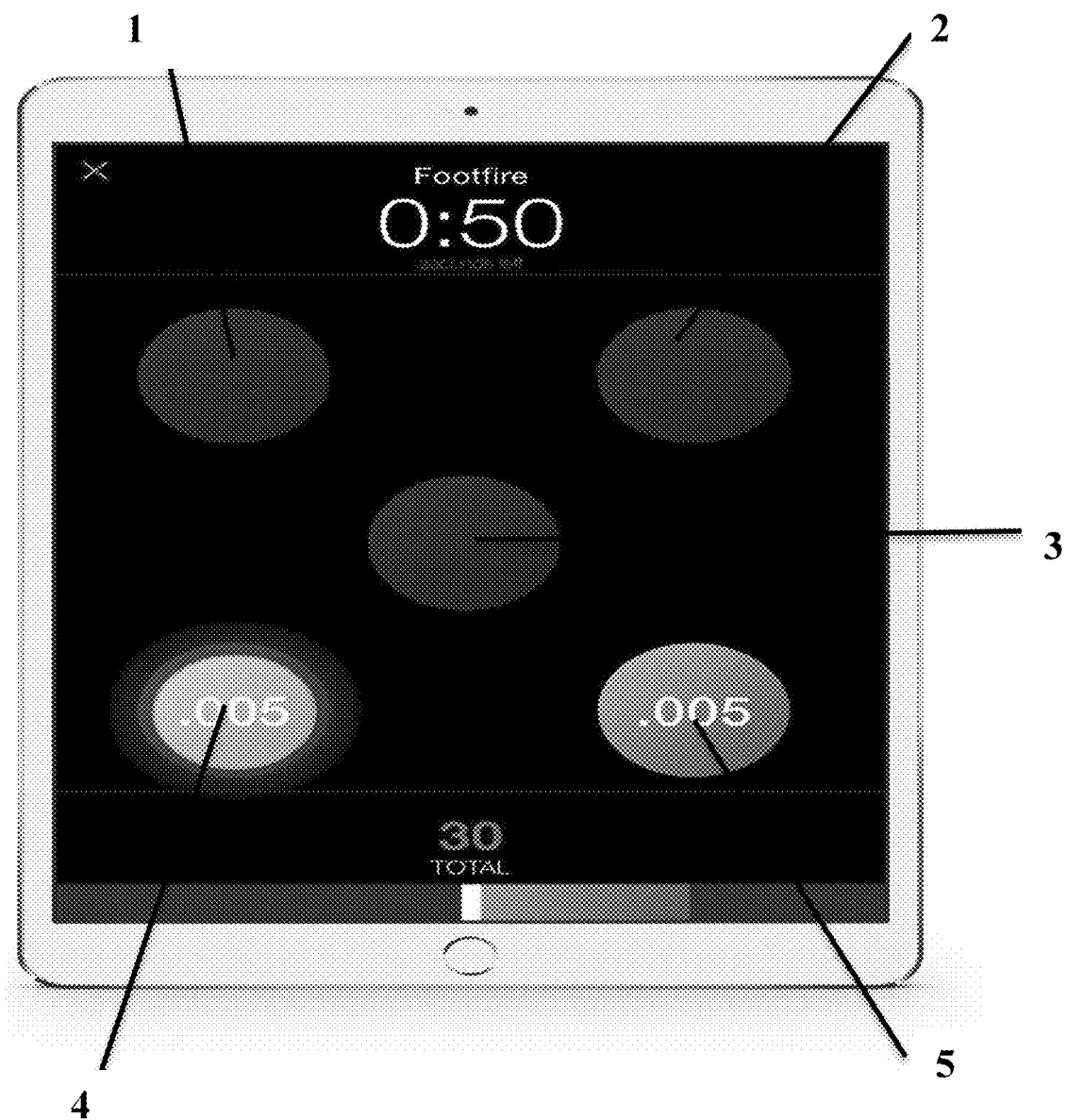
FIG. 29 shows an embodiment of a mobile app screen of an execution function for use in the system.

FIG. 29 shows an exemplary screen for an execution function in a mobile app version of the system 1000. The execution screen is a visual representation of the sensor areas. Exercises can be executed with the following response modes: AR Board Lite Version, AR Board Extended Version (with wearable data), Sensor Board with Bluetooth, and Touch Screen.

Each on-screen sensor can have various states.
Disabled: if a sensor is inactive and an athlete/patient cannot press it, then the sensor is dimmed or greyed out on screen.
Highlighted: if a user can interact with a sensor, then the sensor is highlighted on screen with a specific color.
Pressed: if a sensor is pressed, the corresponding on-screen sensor area gets an embossed effect to give feedback to the user that the sensor is pressed.

Real-time feedback to the user is critical to enhance performance and rehabilitation and increase the likelihood of the training or rehabilitation transferring to daily activities such as sports, recreation, walking, and running. Quick Board's software provides unique capabilities to elicit transferable performance and rehabilitation changes. It is also imperative to provide visual, real-time feedback to address neuroplastic effects of injuries.

Contact and Reaction times are displayed in real-time on corresponding on-screen sensor locations. Depending on the exercise being performed, contact times or reaction times are displayed on the screen in real-time which appear on the screen sensor locations being pressed by the athlete/patient. Providing athletes/patients the ability to see their contact times or reaction times in real-time during exercises enables them to modify their performance based on the visual feedback provided. For example, when contact times are displayed, an athlete/patient can see if they are favoring a leg and shift more weight on their other leg to make their contact times more even. In order to improve function, an athlete/patient's foot should not be on the ground very long. By displaying contact time in real-time, Quick Board's software teaches athletes/patients to quickly execute touches, reduce ground contact time, and maintain symmetry.

Progress Bar Capability based on sensor board or wearable data:
At the bottom of the execution screen, a real-time progress bar is displayed. The progress bar has two types of functionality:
1. Progress bar is displayed at the bottom of the screen which compares the athlete/patient's right and left leg performance during an exercise. Progress bar reflects performance based on, but not limited to, ground contact times, foot pressure, cadence, impulse, impact force, reaction times.
Progress bar can reflect an average of the performance time or the most recent metric recorded. Progress bar scale is calculated by using the standard deviation of the athlete/patient's symmetry performance history for that exercise. Progress bar function initiates from the middle of the screen. Progress bar reflects symmetry performance by displaying a red bar to the right or left which communicates to the athlete/patient whether their right or left side is underperforming.
2. Progress bar compares athlete/patient progress to a set metric. An athlete/patient's progress is reflected during the exercise compared to their worst result, average result, or best result.
Progress bar can also be set to reflect an athlete/patient's progress versus a worst result, average result, or best result of a population, ie facility or location, region, country, gender, age, sport, position, injury, procedure, degenerative disease, or any other filters to accurately compare the athlete/patient to a relevant population.
Progress bar function initiates from the middle of the screen. The bar will turn red and increase in length to the left if the athlete/patient is falling behind the set comparison. It will turn green and increase in length to the right if the athlete/patient is well ahead of the set comparison. The progress bar is not visible, or only slightly visible, if the user is on pace to match the set comparison.

All of the exercise types below can be executed with the following response modes: AR Board Lite Version, AR Board Extended Version (with wearable data), Sensor Board with Bluetooth, and Touch Screen.

1. COUNT Exercises

In a count exercise, the athlete/patient will see the sensors they can interact with, some of the sensor areas could be disabled. When the exercise starts they will try and complete as many touches until the exercise ends. There are no incorrect touches in this type of exercise.

Some count exercises will show the number of touches individually for each leg. This helps in discovering imbalances in the athlete's execution.

2. SEQUENCE Exercises

Similar to count, the athlete/patient is trying to get as many touches as possible. They will see the sensor areas they can interact with, but the sensor areas have to be pressed in a certain predetermined sequence (for example, pressing the following sensors: center sensor (right leg), top left sensor (left leg), center sensor (right leg), bottom left sensor (left leg) and then repeating this sequence as fast as possible).

In this type of exercises if an incorrect sensor area has been pressed, the athlete/patient will get +1 ERROR and the next sensor area to be pressed will be highlighted. Sequence exercises show the number of touches and errors in real-time during the exercise.

The same real-time performance indicators (i.e. live contact time over the onscreen sensor areas and live progress bar on the bottom of the screen) are present for sequence exercises.

3. REACT Exercises

Similar to sequence exercises, the athlete/patient must focus on the device screen to see which on-screen sensor area is highlighted and press the corresponding sensor area.

The difference is that, for react exercises, the order that the on-screen sensors are highlighted is not predetermined. The athlete/patient doesn't know which sensor area to press next.

Additionally, for each sensor area, the system 1000 provides reaction times over the onscreen sensor areas. An athlete/patient can see left side reaction times and right side reaction times so they know which sensors they must react to faster.

4. AGILITY Exercises

Agility exercises are used without the board. The athlete/patient has to perform certain types of physical exercises, such as running, jumping, or other activities set by the admin/location administrator. On the screen, an athlete/patient can see two types of info: arrows—for showing the athlete in which direction they have to move, and squares with a descriptive text explaining what action needs to be performed (eg: jumping).

5. VERTICAL Exercises

The device starts up by showing the athlete/patient the starting position. After the athlete/patient is set in the instructed starting position, they see a message instructing them to jump whenever they are ready. After the athlete/patient jumps, they can see in real time the time spent in the air. The timer stops when the athlete/patient lands on the sensor areas again. Depending on the exercise, the athlete/patient will perform multiple jumps. For multiple jump exercises, the athlete/patient can see their time spent in the air and time spent on the sensor areas between jumps. The system uses the time spent in the air to calculate the height of the user's vertical jump.

Figure 31:
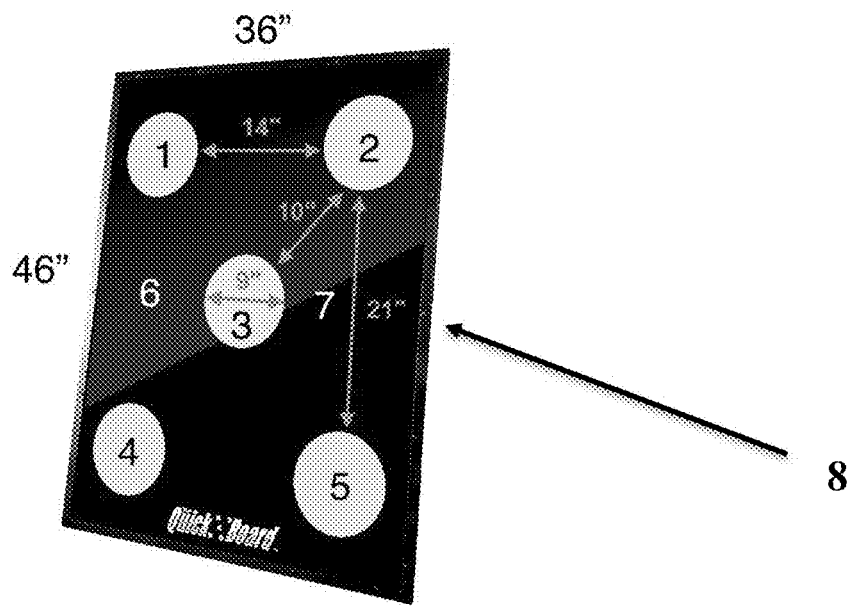
FIG. 31 shows an embodiment of a virtual sensor board layout for display on a screen for use in the system, and including dimensions of a large size board option.

In embodiments, the user has the option to select between different sizes of virtual sensor boards. In embodiments, the system can recommend a virtual sensor board size based on performance data and the user's abilities. FIG. 31 shows an embodiment of a virtual sensor board 8 layout for display on a screen for use in the system. The drawing shows dimensions of a large size virtual sensor board option. It should be noted the image of the board fits the size of the tablet, but that the operative board on the floor (which exists only virtually, as indicated in the tablet image of FIG. 38) replicates the dimensions shown in the drawing. In other words, when the user moves his or her feet with reference to the image of the board shown on the tablet 11, the user must move his or her feet according to the dimensions indicated in the drawing. In this embodiment, the board is 46 inches tall and 36 inches wide. The virtual sensors 1, 2, 3, 4, 5 are 9 inches in diameter. The top left and top right virtual sensors 1 and 2 are spaced 14 inches apart, as are the bottom left 4 and bottom right 5 virtual sensors. The top right and bottom right virtual sensors 2 and 5 are 21 inches apart, as are the top left 1 and bottom left 4 virtual sensors. The center virtual sensor 3 is 10 inches from each of the outer sensors 1, 2, 4, 5.

Figure 32:
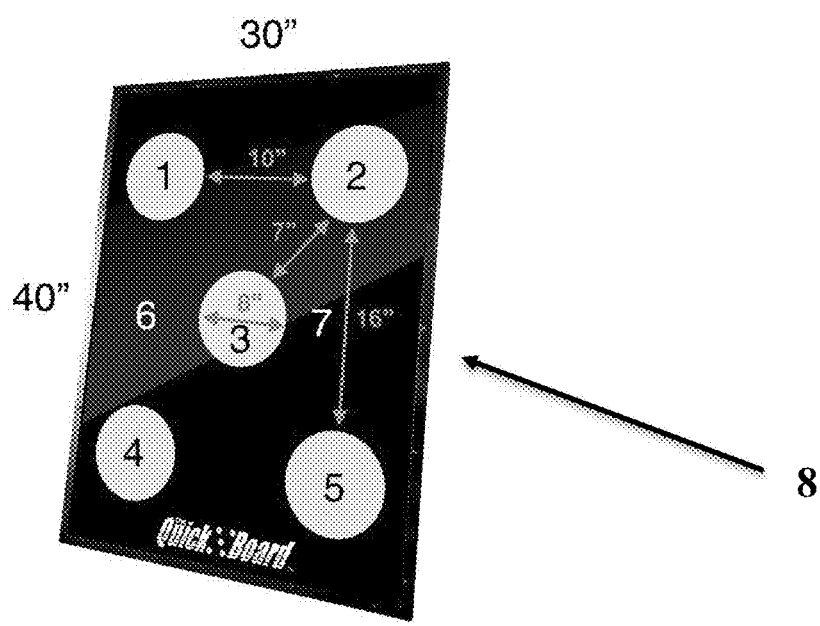
FIG. 32 shows an embodiment of a virtual sensor board layout for display on a screen for use in the system, and including dimensions of a small size board option.
Figure 33:
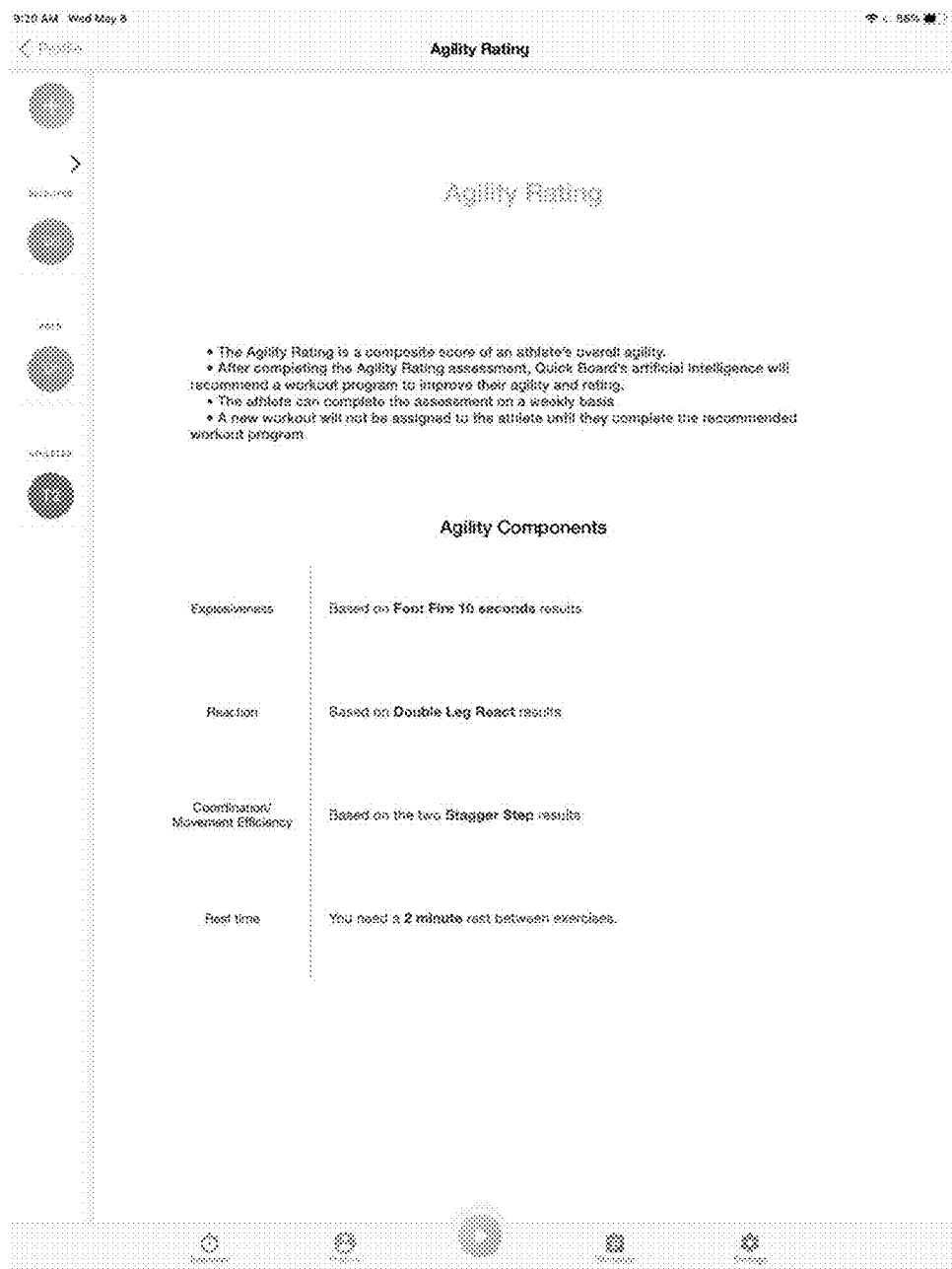
FIG. 33 shows an embodiment of a screen for an agility rating summary for use in the system.
Figure 34:
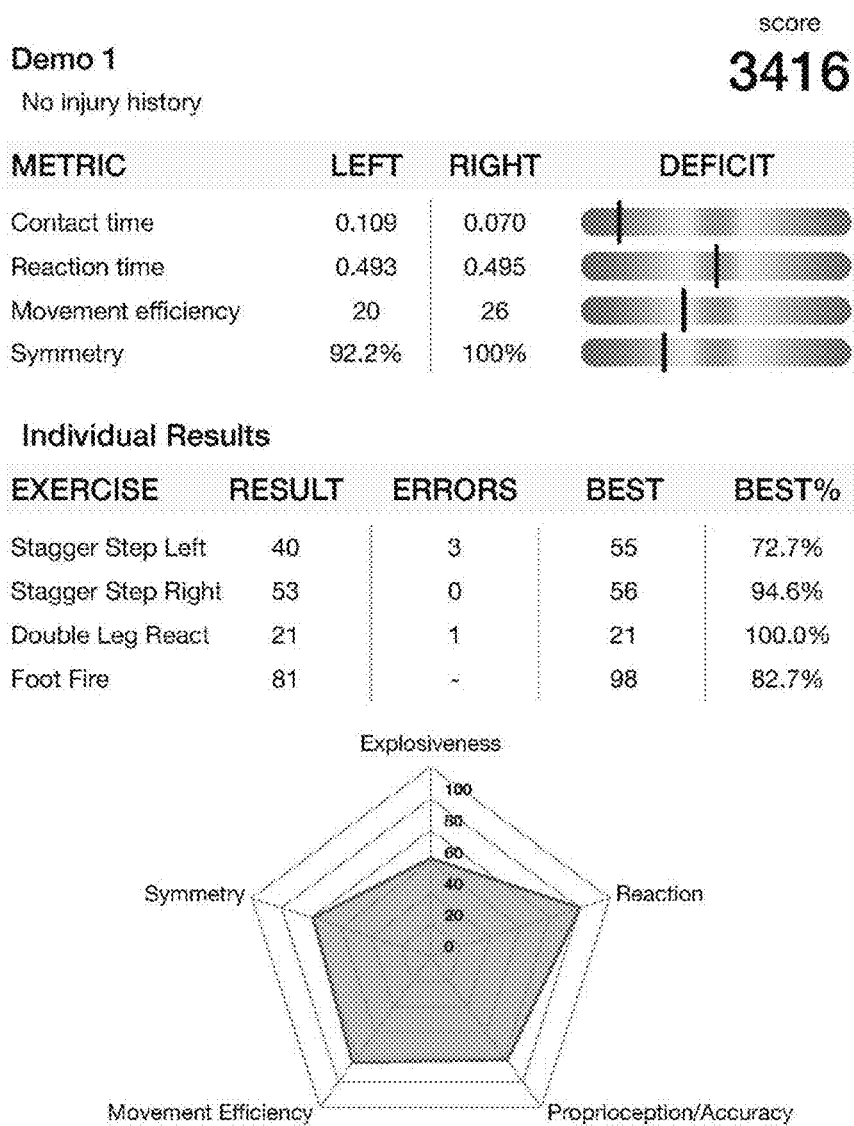
FIG. 34 shows an embodiment of a screen for an agility rating report for use in the system.

FIG. 32 shows an embodiment of a virtual sensor board layout for display on a screen for use in the system having smaller dimensions than the embodiment of FIG. 31. In this embodiment, the board is 40 inches tall and 30 inches wide. The virtual sensors 1, 2, 3, 4, 5 are 8 inches in diameter. The top left and top right virtual sensors 1 and 2 are spaced 10 inches apart, as are the bottom left 4 and bottom right 5 virtual sensors. The top right and bottom right virtual sensors 2 and 5 are 16 inches apart, as are the top left 1 and bottom left 4 virtual sensors. The center virtual sensor 3 is 7 inches from each of the outer sensors 1, 2, 4, 5.

While variations can be made in the foregoing dimensions and relationships, it should be appreciated that the layout and the dimensions of the board are important to the performance of the system in using the various drills described herein.

Although the system has been described with reference to virtual sensor boards, it should be appreciated that the routines and features of the system 1000 can be adapted for use with physical embodiments of sensor boards.

Figure 30:
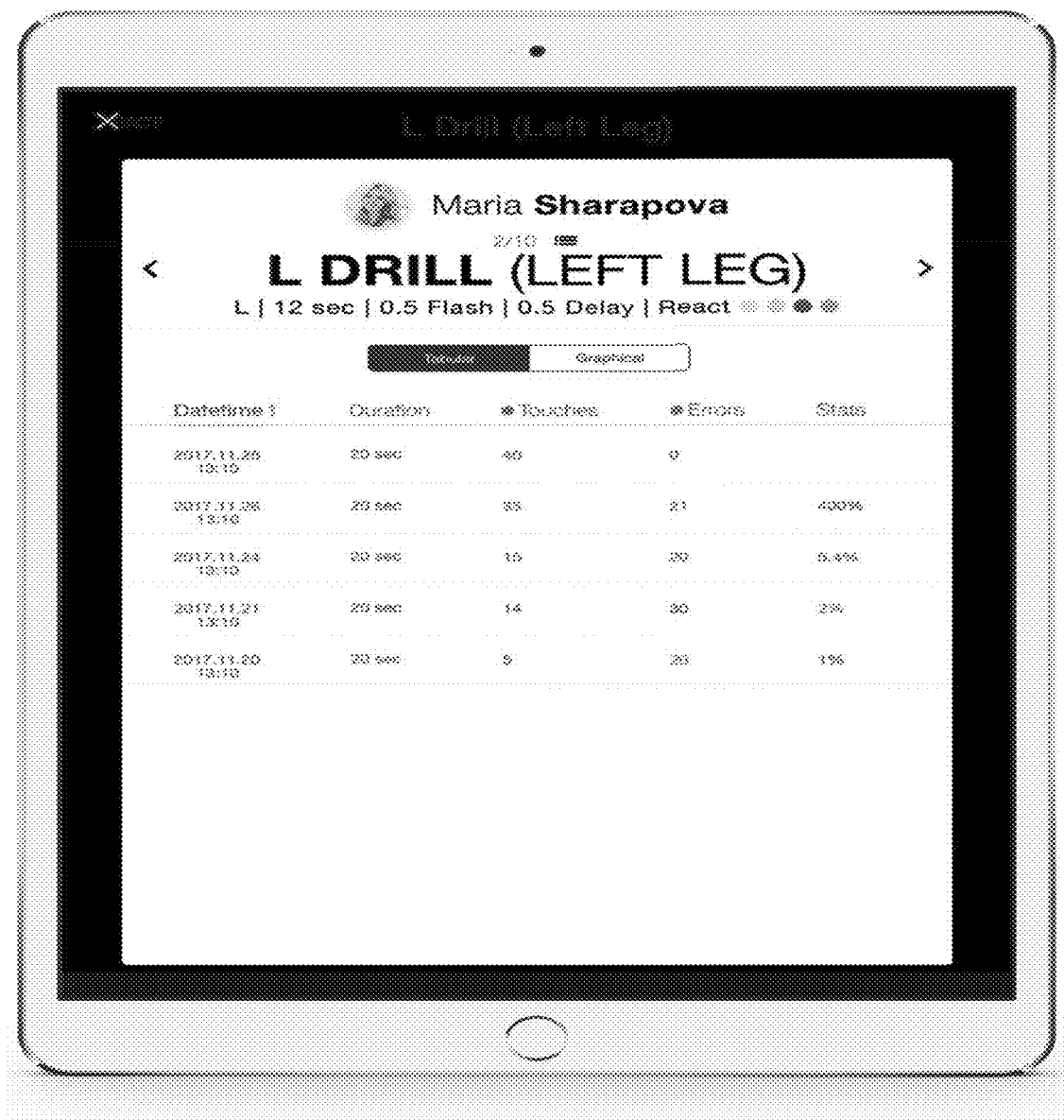
FIG. 30 shows an embodiment of a mobile app screen of save and comparison function for use in the system.

FIG. 30 shows an exemplary screen for a save and comparison function in a mobile app version of the system 1000. Save and Comparison is shown after an activity (exercise, playlist, workout) has ended. Depending on how many athletes/patients participated in the activity, there are two types of results: one user: comparison of the athlete/patient's activity over time; two or more users: comparison between the athletes/patients.

In the upper part athletes/patients can move through each exercise that has been performed, either by pressing the arrows or the playlist icon. There are two types of results, tabular, showing all data in a table, or graphical, visual illustration represented as a chart.

The data that will be shown in the table in the following format:
  datetime: date and time when the exercise was performed.
  duration: how long the exercise lasted.
  touches: the total number of touches that were successfully pressed.
  errors: total number of misses or incorrect touches.
  stats: % Change, % Deficit For exercises that end after a fixed time period, the result is determined by the number of touches. The more touches the athlete/patient managed to get, the better the result.

For exercises that end after a predetermined number of touches, the result is based on the time it took the athlete/patient to complete the exercise. The faster the athlete/patient completed the exercise, the better the result.

For neurocognitive react exercises, the system 1000 compares the athlete/patient's average reaction time.

Some exercises may be paired together, in which case the comparison is done between the paired exercises results, not between the latest exercise result and previous ones. For example, a paired exercise may have a couple of exercises, each testing one of the athlete/patient's individual legs exclusively. For that exercise, the comparison is done between the left leg result and right leg result. The goal of paired exercises is usually to identify and quantify bilateral imbalances.

On vertical exercises, the system 1000 compares an athlete/patient's air time or average air time for vertical exercises with multiple jumps.

Reimbursement

In the current healthcare environment, providing objective outcomes is critical for payer reimbursement. The system 1000 can establish outcome ratings systems based on patient population norms (age, gender, activity level), injury, procedure performed (e.g. ACL procedures: hamstring tendon graft, patellar tendon graft, allograft), medical device implants used, etc.

Injury ratings will be produced during rehab based on progress compared to similar population data with the same injury. Injury ratings can be filtered down by the same criteria as outcomes. Outcome ratings are calculated towards the end or at the end of rehab. Estimated outcome rating can be provided throughout rehab based on algorithms and relevant population data to give a doctor and therapist an idea of patient's progress. Injury and outcome ratings could also take into account normative data. Additionally, the software 1100 generates reports after each visit. The reports can be transmitted as progress reports to the patient's electronic medical record (EMR) and to the payer.

In summary, distinguishing features of the system 1000 include: used with patients in the clinic, between visits, and remotely; software will automatically take a patient through a protocol without or limited supervision and save data to their profile. Program rest time, exercises/protocol (practitioner customizes or software will provide exercises/protocol based on population and injury), displays patient or clinic previous best for that exercise (optional to provide clinic best based on patient population norms, injury/disease, activity level, procedure, medical device; the system 1000 AI uses machine learning to automatically generate next session protocol, which is a progression, regression, or equivalent difficulty of the protocol performed last. Exercises can be the same but with a different exercise length, i.e. more/less time or touches programmed; patients receive injury ratings based on progress and/or assessment protocol; system 1000 software generates injury rating, estimated outcome rating based on population norms, and outcome rating; Patient reports are generated after each session at home and in clinic. Reports are uploaded to EMR and submitted to payer; creation of augmented reality to replace sensor board using cameras or wearable devices, while retaining the function and benefits of a sensor board.

The components of the system 1000 may be arranged in a convenient format, such as in box containing the components. However, the components of the system 1000 do not have to be packaged or delivered together, provided that they are assembled or collected together for use at the time of exercise or physical therapy.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A system for providing physical training routines for a user via a virtual sensor board on a display and on a floor, the system comprising:
   a tablet device having a processor and a display, the processor having a computer readable medium programmed to administer a physical training routine program to the user via the display;
   the physical training routine program configured to display a virtual sensor board on the display, the virtual sensor board including a plurality of virtual sensor units for indicating locations for foot touches by said user on said floor, the plurality of sensor units including a center sensor unit and at least four peripheral sensor units spaced peripherally from the center sensor unit, the virtual sensor board replicating a floor virtual sensor board located on said floor;
   a pair of wearable devices for executing a physical training routine and collecting user physical data during the physical training routine and transmitting user physical data to the tablet device, each of the wearable devices attachable to a foot or shoe of said user, the user physical data comprising foot touches of the user on a floor surface relative to changes on the virtual sensor board on the display;
   a camera system for executing an augmented reality physical training routine and collecting visual user data during the routine and for transmitting the visual user data to the tablet device; and
   the physical training routine program configured to process the user physical data and the user visual data to administer physical training functionalities, administering physical training functionalities including varying an appearance of the virtual sensor units on the virtual sensor board to correspond with target physical touch areas on the floor virtual sensor board and foot touches registered on the floor virtual sensor board.

2. The system of claim 1, wherein the tablet is in two-way communication with higher level system components, the higher level components including an external processor configured to process user data and an external database configured to store user data.

3. The system of claim 2, wherein the higher level components are cloud-based.

4. The system of claim 1, wherein the camera system for executing augmented reality physical training routines is combined with:
   a video processing algorithm for tracking said user's shoes, the algorithm for tracking said user's shoes comprising tracking-learning-detection; and
   a video processing algorithm for detecting the presence of said user's shoes on the sensor area, said algorithm for detecting the presence of said user's shoes on the sensors area using background change.

5. The system of claim 1, wherein the physical training functionalities include user metrics comprising Cadence; Foot strike; Pressure; Impulse; Impact force; Contact time; Air time; Pronation; and Supination.

6. The system of claim 1, wherein the physical training routine program administers physical training programs that train speed, quickness, strength, stability, reaction, coordination, proprioception, mobility, and balance.

7. The system of claim 1, wherein the physical training routine program displays real-time feedback on the display during administration of physical training programs.

8. The system of claim 1, wherein the wearable device is a sub-insole device that adheres to the bottom of an insole.

9. The system of claim 8, wherein the sub-insole device includes a plurality of pressure sensors.

10. The system of claim 1, wherein the physical training routine program generates user ratings and reports based on user data.

11. The system of claim 1, wherein the physical training routine program administers physical training programs comprising automated workouts based on user data.

12. The system of claim 2, wherein the systems administers multi-location database capabilities.

* * * * *